US012606670B2

(12) United States Patent
Rhonè et al.

(10) Patent No.: US 12,606,670 B2
(45) Date of Patent: Apr. 21, 2026

(54) COMPOSITION COMPRISING ACTIVATED AND FUNCTIONALIZED PREPOLYMER

(71) Applicant: TISSIUM SA, Paris (FR)

(72) Inventors: Benoit Rhonè, Mantes la Jolie (FR); Camille Legros, Paris (FR); João Reina Maia E Silva, Paris (FR); Prune Gerbouin, Paris (FR); Maria Pereira, Lisbon (PT)

(73) Assignee: TISSIUM SA, Paris (FR)

( * ) Notice: Subject to any disclaimer, the term of this patent is extended or adjusted under 35 U.S.C. 154(b) by 1032 days.

(21) Appl. No.: 17/755,237

(22) PCT Filed: Oct. 23, 2020

(86) PCT No.: PCT/EP2020/079941
§ 371 (c)(1),
(2) Date: Apr. 25, 2022

(87) PCT Pub. No.: WO2021/078962
PCT Pub. Date: Apr. 29, 2021

(65) Prior Publication Data
US 2022/0380531 A1 Dec. 1, 2022

(30) Foreign Application Priority Data
Oct. 25, 2019 (EP) .................................... 19315131

(51) Int. Cl.
*C09J 167/02* (2006.01)
*A61L 24/04* (2006.01)
*C08G 63/91* (2006.01)

(52) U.S. Cl.
CPC .......... *C08G 63/914* (2013.01); *A61L 24/046* (2013.01); *C09J 167/02* (2013.01)

(58) Field of Classification Search
CPC ..... C08G 63/914; A61L 24/046; C09J 167/02
(Continued)

(56) References Cited

U.S. PATENT DOCUMENTS 6,011,103 A 1/2000 Inoue
2013/0071930 A1* 3/2013 Chu ........................ C08G 63/91 525/379
2017/0121454 A1* 5/2017 Saltzman .............. C12P 13/001

FOREIGN PATENT DOCUMENTS

JP 2009-523864 A 6/2009
JP 2018519409 A 7/2018
(Continued)

OTHER PUBLICATIONS

Hunghao Chu et al., "Design, synthesis, and biocompatibility of an arginine-based polyester", Biotechnology Progress, vol. 28, No. 1, Oct. 2011, pp. 257-264. (Year: 2011).*
(Continued)

*Primary Examiner* — Joseph S Del Sole
*Assistant Examiner* — Ronald Grinsted
(74) *Attorney, Agent, or Firm* — Finnegan, Henderson, Farabow, Garrett & Dunner, LLP

(57) ABSTRACT

A composition comprising a pre-polymer having activated and functionalized groups on a polymeric backbone is disclosed. The composition may be used in a method of adhering or sealing tissue, or for adhering a medical device to the surface of a tissue. The composition has improved adhesive and sealant properties and comprises a pre-polymer comprising a polymeric unit of the general formula $(\text{-A-B-})_n$. A represents a substituted or unsubstituted polyol, B represents a substituted or unsubstituted polyacid, and n represents an integer greater than 1. Additionally, the composition has a zeta potential in the range of 0 to 45 mV.

31 Claims, 8 Drawing Sheets

(58) Field of Classification Search
USPC .......................................................... 528/292
See application file for complete search history.

(56) References Cited

FOREIGN PATENT DOCUMENTS

| | | | |
|---|---|---|---|
| WO | 199731045 | 8/1997 | |
| WO | WO-2018057649 A1 * | 3/2018 | ........... A61K 31/704 |

OTHER PUBLICATIONS

Huang et al., "Phosphorylated poly(sebacoyl diglyceride)—a phosphate functionalized biodegradable polymer for bone tissue engineering", (J. Mater. Chem. B, 2016, v.4, pp. 2090-2101) (Year: 2016).*
H. Chu et al., "Design, Synthesis, and Biocompatibility of an arginine-based polyester", Biotechnology Progress, vol. 28, No. 1, 27 Oct. 27, 2011, pp. 257-264.
International Search Reported date of mailing Jan. 19, 2021, for corresponding application No. PCT/EP2020/079941 filed Oct. 23, 2020.
Written Opinion Of The International Searching Authority, for corresponding application No. PCT/EP2020/079941 filed Oct. 23, 2020.

* cited by examiner

C1.0 C1.1 C1.2 C1.3 C1.4

C1.0

C1.1

C1.5

C1.0

C1.1

C1.6

C1.0

C1.9

C1.10

C1.1

C1.8

C1.1

C1.7

C2.0

C2.2

C2.2

C2.3 / C2.4

C1.0

C1.11

C1.12

COMPOSITION COMPRISING ACTIVATED AND FUNCTIONALIZED PREPOLYMER

CROSS-REFERENCE TO RELATED APPLICATION

This is a National Phase Entry of International Application No. PCT/EP2020/079941, filed Oct. 23, 2020, which claims the benefit of priority to European Patent application Ser. No. 19/315,131.3, filed Oct. 25, 2019, the contents of which are incorporated herein by reference in their entireties.

FIELD OF INVENTION

The present invention relates to a composition comprising an activated and functionalized pre-polymer, a method of manufacturing the composition, a method of curing the composition, a cured composition obtainable therefrom, uses of the composition and methods of using the composition.

BACKGROUND OF THE INVENTION

Open heart surgery typically relies on a suture-based closure or attachment of cardiovascular structures. However, this can be technically challenging due to the fragility of young infant tissue and diseased or damaged adult tissue, leading to longer operative times, increased risk of complications of bleeding or dehiscence, and therefore worse outcomes. Furthermore, cardiopulmonary bypass (CPB) is required for open heart surgery, and this has significant adverse effects, including an inflammatory response and potential neurological complications.

While catheter-based interventions for closure of cardiac defects such as atrial and ventricular septal defects (ASDs and VSDs) have recently emerged in an effort to reduce the invasiveness of the procedures, major challenges remain with securing devices inside the beating heart. Specifically, fixation of devices for catheter-based closure of cardiac septal defects currently relies on mechanical means of gripping tissue. This can cause injury to critical structures, such as heart valves or specialized conduction tissue. Furthermore, if inadequate tissue rims exist around defects, the prosthesis may dislodge, damaging the neighboring structures and also leaving residual defects, limiting device application. Therefore, such methods can only be applied in select patients, depending on the anatomic location and the geometric shape of the defect.

Soft and compliant tissue adhesives that cure rapidly could be used to attach tissue surfaces together or prosthetic devices to tissue without the need for mechanical entrapment or fixation, thereby avoiding tissue compression and erosion. Such materials could find a broad range of applications not only in minimally invasive cardiac repair, but also in the repair of soft tissues potentially with minimal scarring and damage. For example, in vascular surgery, suture-based anastomosis does not always result in an instantaneous hemostatic seal and can create irregularities in the endothelium that predispose to thrombosis. Furthermore, the presence of permanent sutures can cause a foreign body reaction with further inflammation and scarring at the repair site, which may increase the risk of late vessel occlusion. Tissue adhesives could accomplish such repairs with an instantaneous seal and with minimal scarring or tissue damage.

Current clinically-available adhesives, such as medical grade cyanoacrylate (CA) or fibrin sealant, are easily washed out or cured under dynamic wet conditions, are toxic and cannot be used internally, and/or exhibit weak adhesive properties such that they cannot withstand the forces inside the cardiac chambers and major blood vessels. Also, many of these adhesives exhibit activation properties that make fine adjustments or repositioning of the devices very difficult. Moreover, many adhesives under development achieve tissue adhesion only through chemical reaction with functional groups at the tissue surface, and thus become ineffective in the presence of blood.

Alternatives to cyanoacrylate have been explored. U.S. Pat. No. 8,143,042 B2 describes biodegradable elastomers prepared by crosslinking a prepolymer containing crosslinkable functional groups, such as acrylate groups. It also discloses that it is desirable to increase the number of free hydroxy groups on the polymer in order to increase the stickiness of the polymer. Increasing the number of hydroxy groups in the backbone also leads to enhanced solubility in physiologic solutions. This suggests that the primary mechanism of adhesion of the polymer is chemical interactions between functional groups, for example free hydroxy groups on the polymer and the tissue to which it is applied. However, this type of chemical interaction becomes ineffective in the presence of body fluids, especially blood, as shown in Artzi et al., Adv. Mater. 21, 3399-3403 (2009).

Similarly, Mandavi et al., 2008*, PNAS,* 2307-2312, describes nanopatterned elastomeric polymer and proposes applying a thin layer of oxidized dextran with aldehyde functionalities (DXTA) to increase adhesion strength of the adhesive by promoting covalent cross-linking between terminal aldehyde group in DXTA with amine groups in proteins of tissue. This adhesion mechanism based essentially on covalent bonding between the radicals generated during the curing process and functional groups of the tissue has several limitations. The use of adhesives with reactive chemistry requires tissue surfaces to be dried prior to application of the pre-polymer, which makes it very challenging to use in cardiac application, such as during emergency procedures. Additionally, reactive chemistry can denature proteins or tissue and promote undesirable immune reaction such as local inflammation which can lead to adhesive rejection. Moreover, reactive chemistry that only bonds to the surface of tissue would likely have lower adhesion as the interface would be more distinct, and thus there would be a mismatch in mechanical properties at the interface between the glue and tissue.

Elastomeric crosslinked polyesters are disclosed in US 2013/0231412 A1. Biodegradable polymers are disclosed in U.S. Pat. No. 7,722,894 B2. Adhesive articles are disclosed in WO2009067482 A1 and WO2014/190302 A1. Blood resistant surgical glue is described in Lang et al. "A Blood-Resistant Surgical Glue for Minimally Invasive Repair of Vessels and Heart Defects," Sci. Transl. Med., 8 Jan. 2014: Vol. 6, Issue 218, p. 218ra6 and WO2014/190302 A1.

SUMMARY OF THE INVENTION

The invention provides an improved and commercially viable activated and functionalized pre-polymer that can be readily applied to the desired site, is biocompatible (non-toxic), and exhibits strong adhesive forces once cured/crosslinked leading to improved tissue sealant/adhesive.

The improved activated and functionalized pre-polymer remains in place at the desired site prior to curing/crosslinking, even in the presence of bodily fluids, such as blood.

The improved activated and functionalized pre-polymer is stable when stored.

More particularly, the invention provides a composition which comprises:

a pre-polymer having activated and functionalized groups on a polymeric backbone, wherein the composition has a zeta potential in the range of from 0 to 45 mV.

The present invention also provides a method for preparing the composition of the present invention.

The present invention further provides a method of curing the composition according to the present invention, comprising curing the composition with a stimulus, for example light in the presence of a photo-initiator.

The present invention also provides a cured composition obtainable by the curing method according to the present invention. Said cured composition is desirably an adhesive, i.e. one that can bind strongly to a surface or can bind one surface to another.

The present invention further provides methods of use and use of the composition according to the present invention for gluing or sealing tissue or for adhering medical device to the surface of tissue.

The inventors have found that, compared to known compositions, the present invention offers advantages which are not found in the prior art.

DETAILED DESCRIPTION OF THE INVENTION

Pre-Polymer

Figure 1:
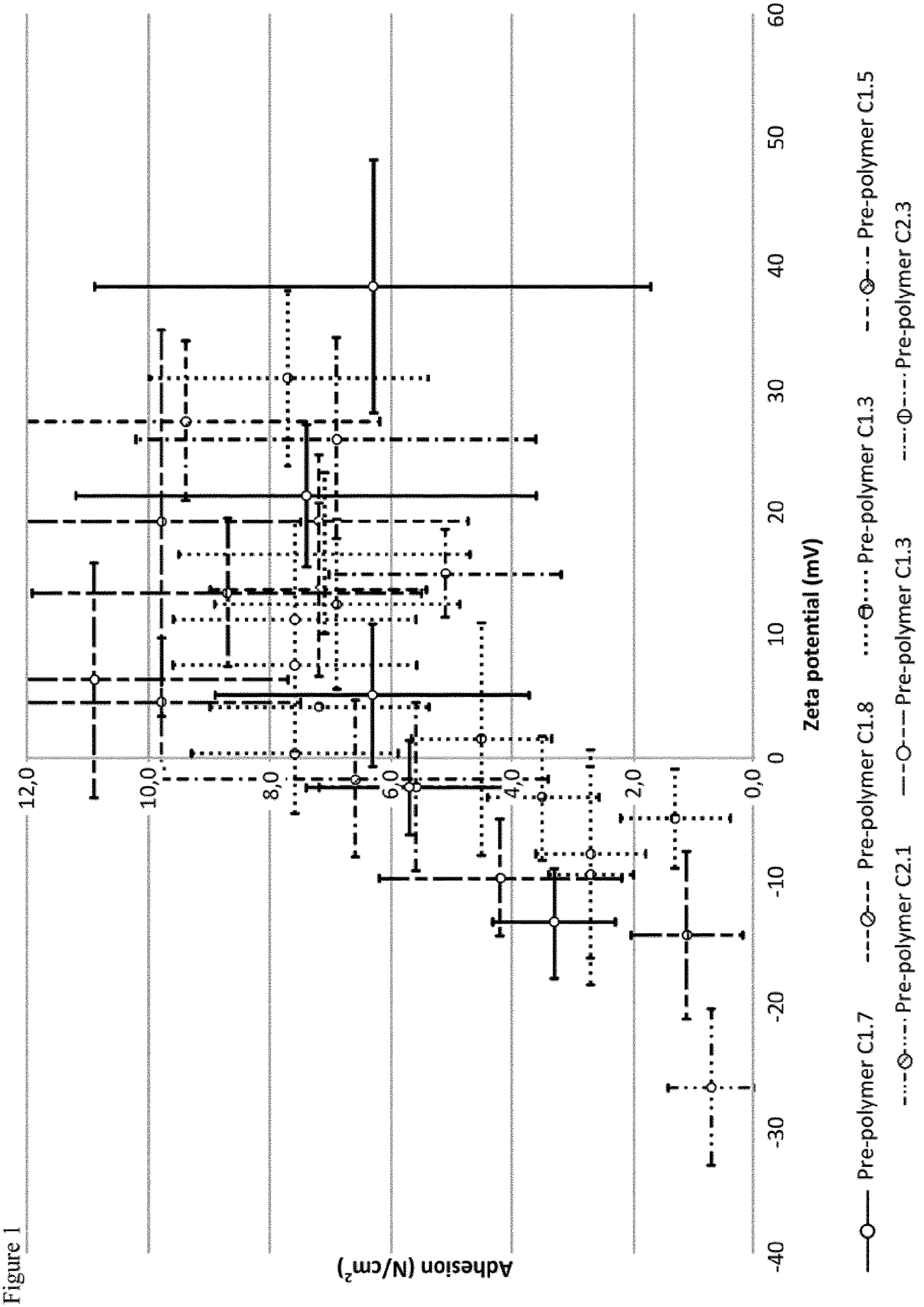
FIG. 1 shows a graph comparing the zeta potential of compositions according to the invention with the adhesion of the composition after curing.
Figure 2:
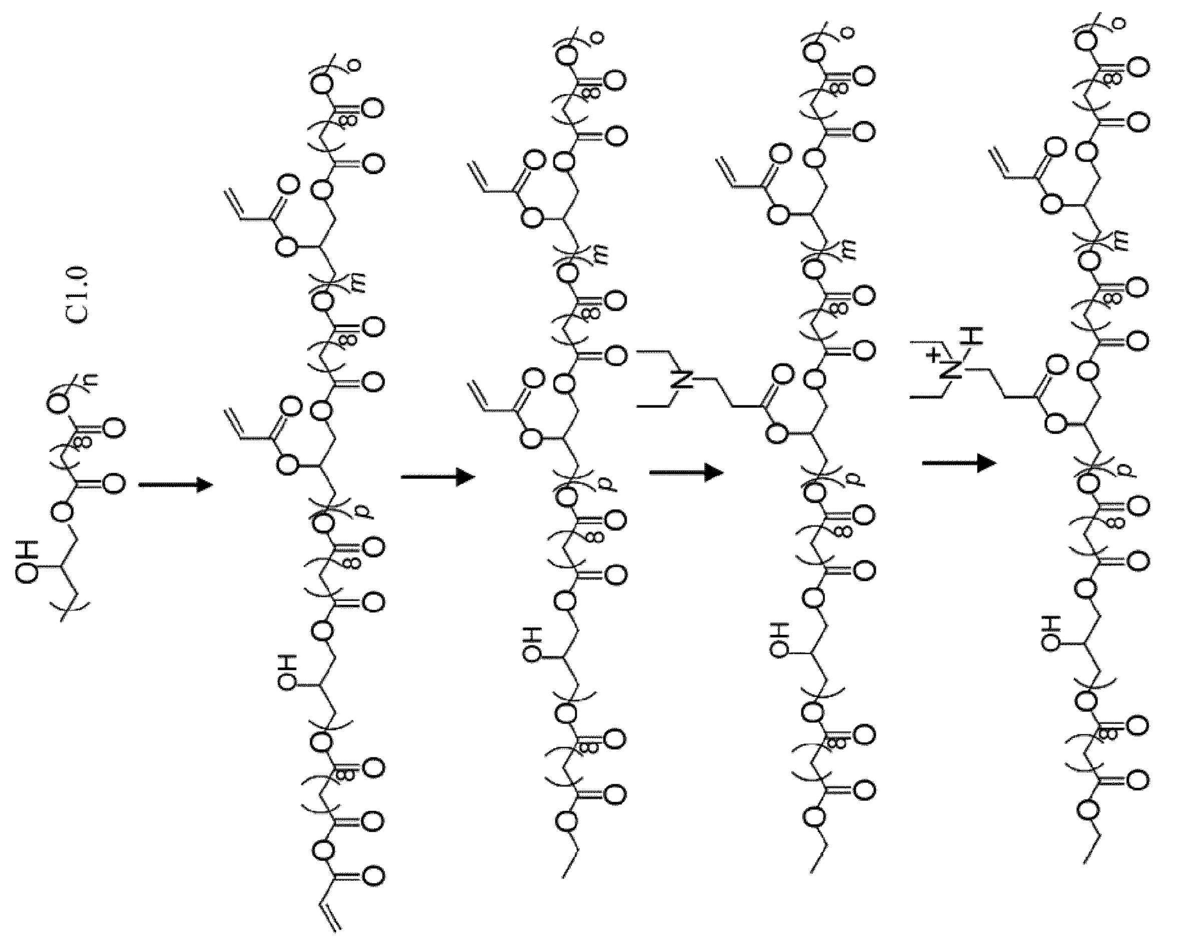
FIGS. 2-8 show the syntheses of compositions according to the invention.
Figure 3:
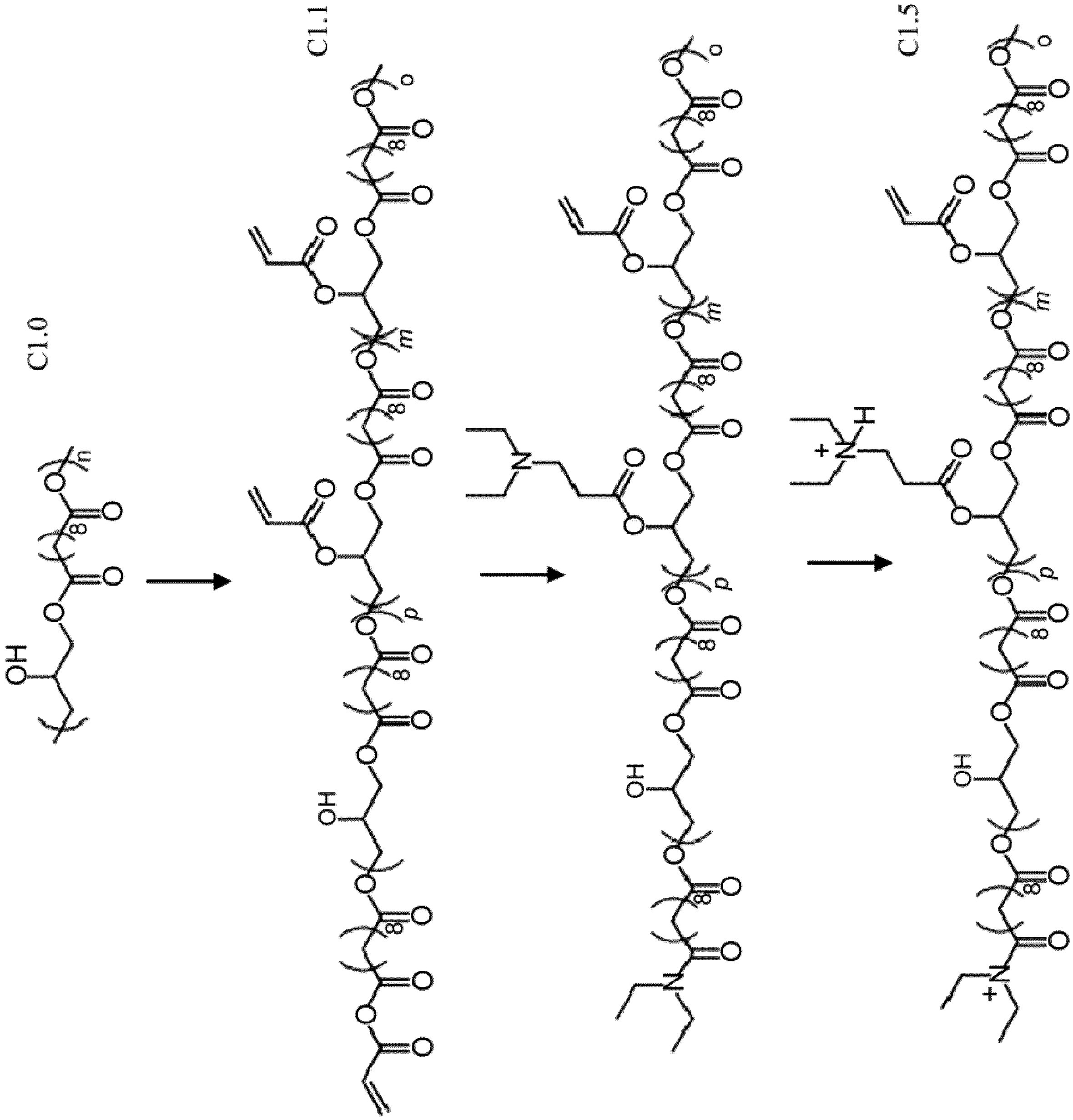
Figure 4:
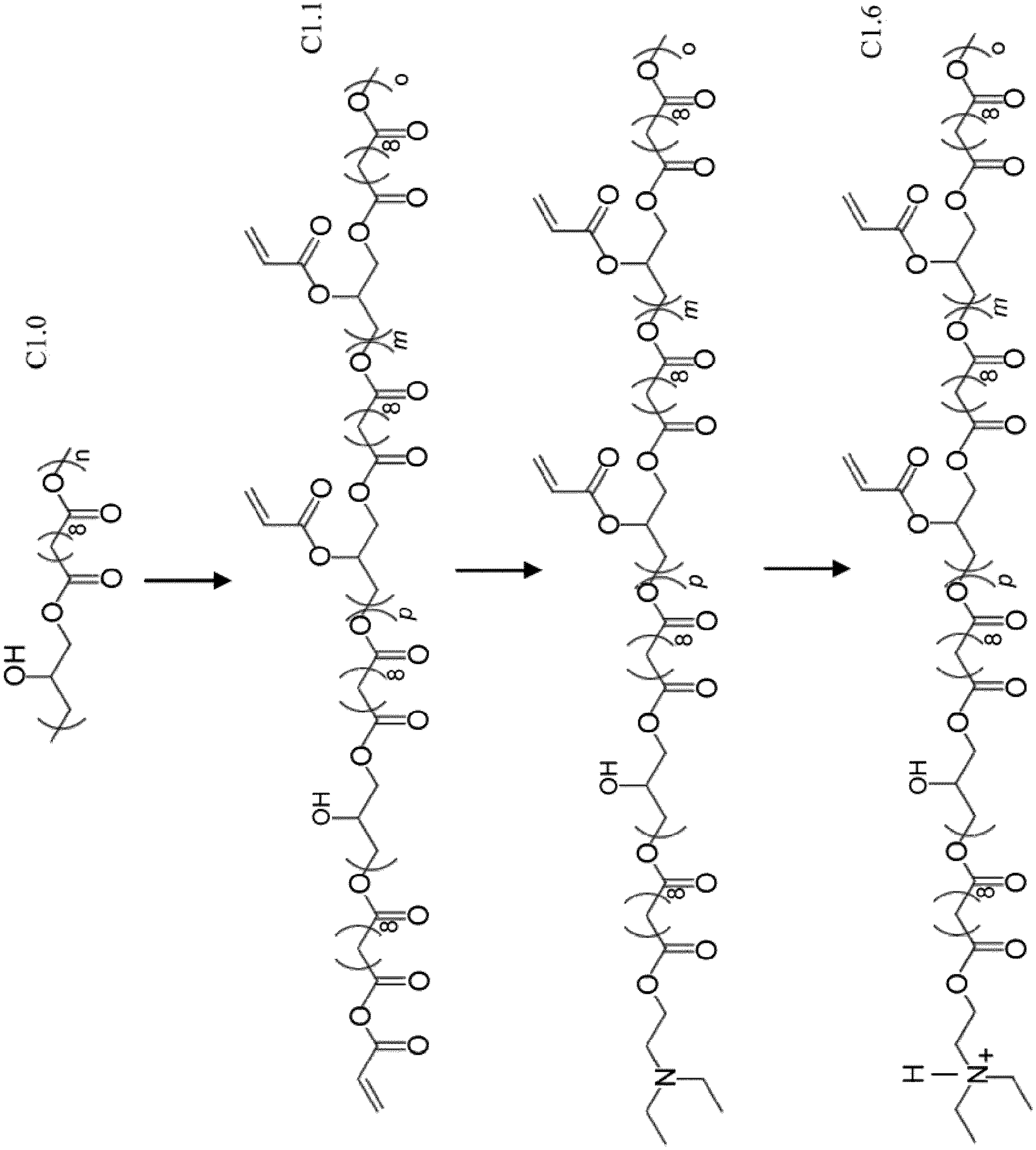
Figure 5:
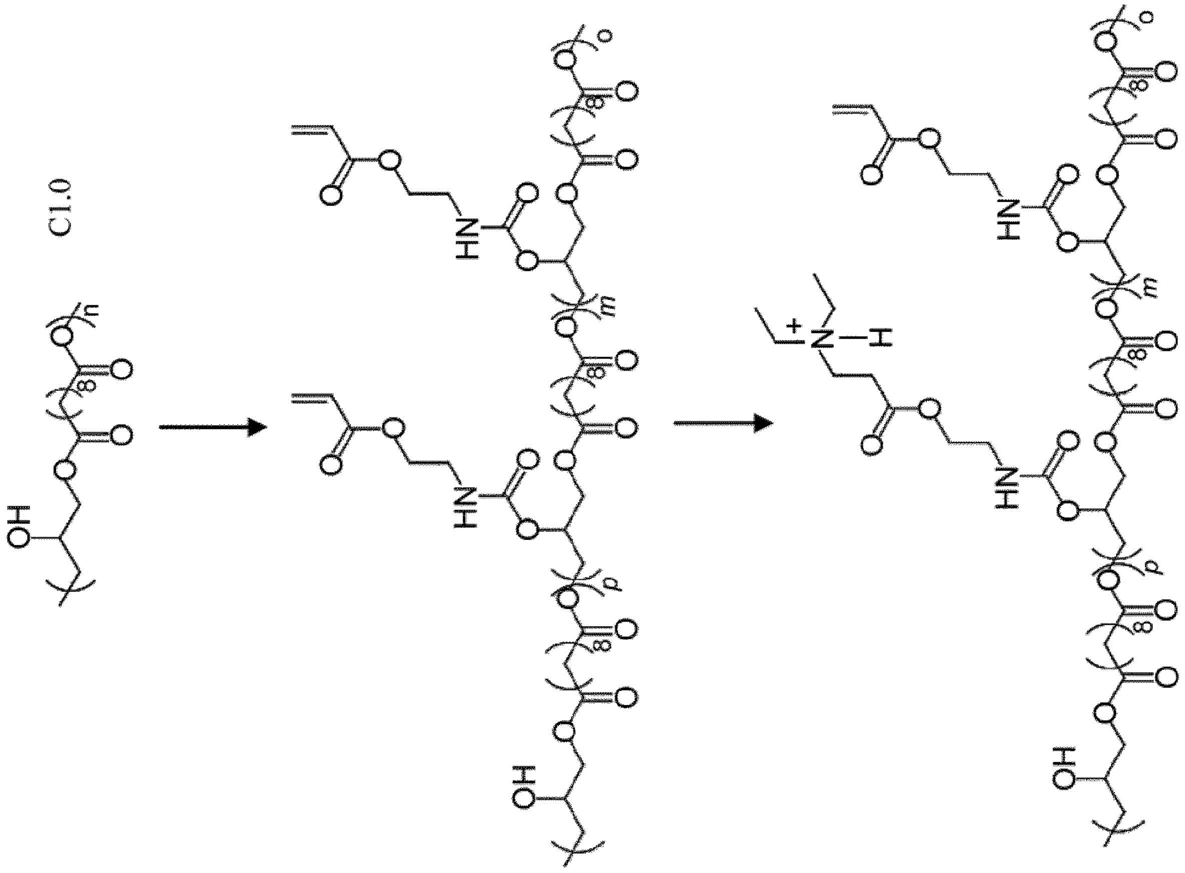
Figure 6:
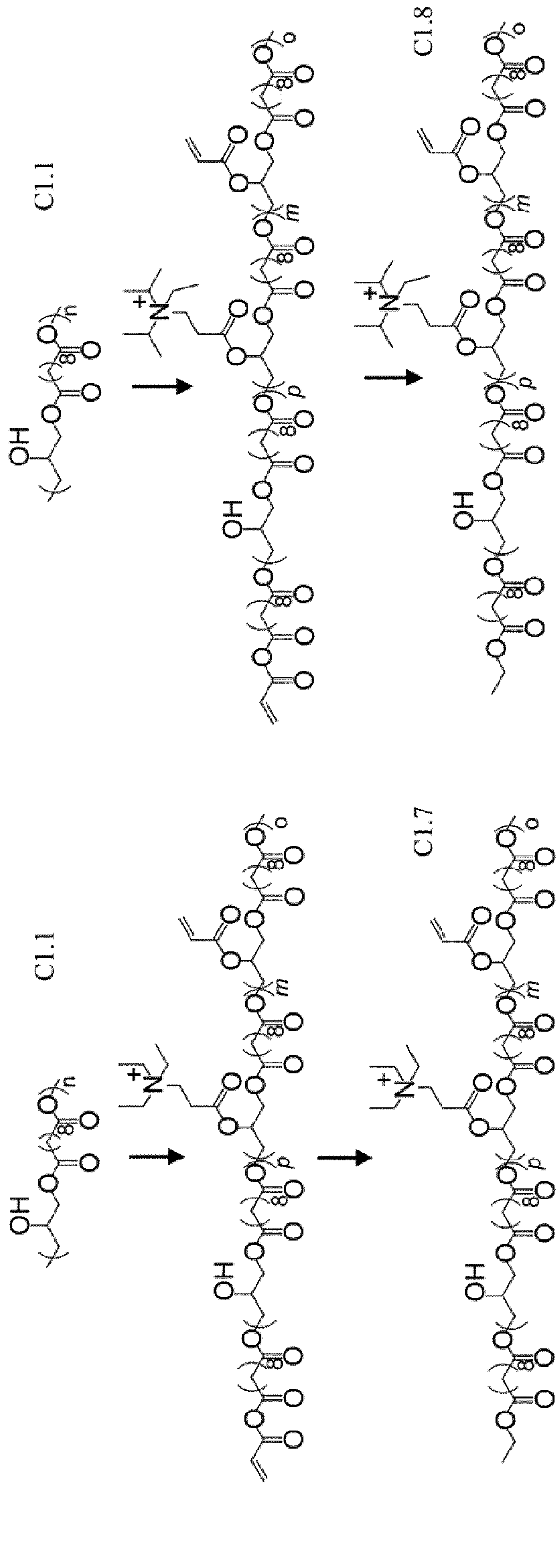
Figure 7:
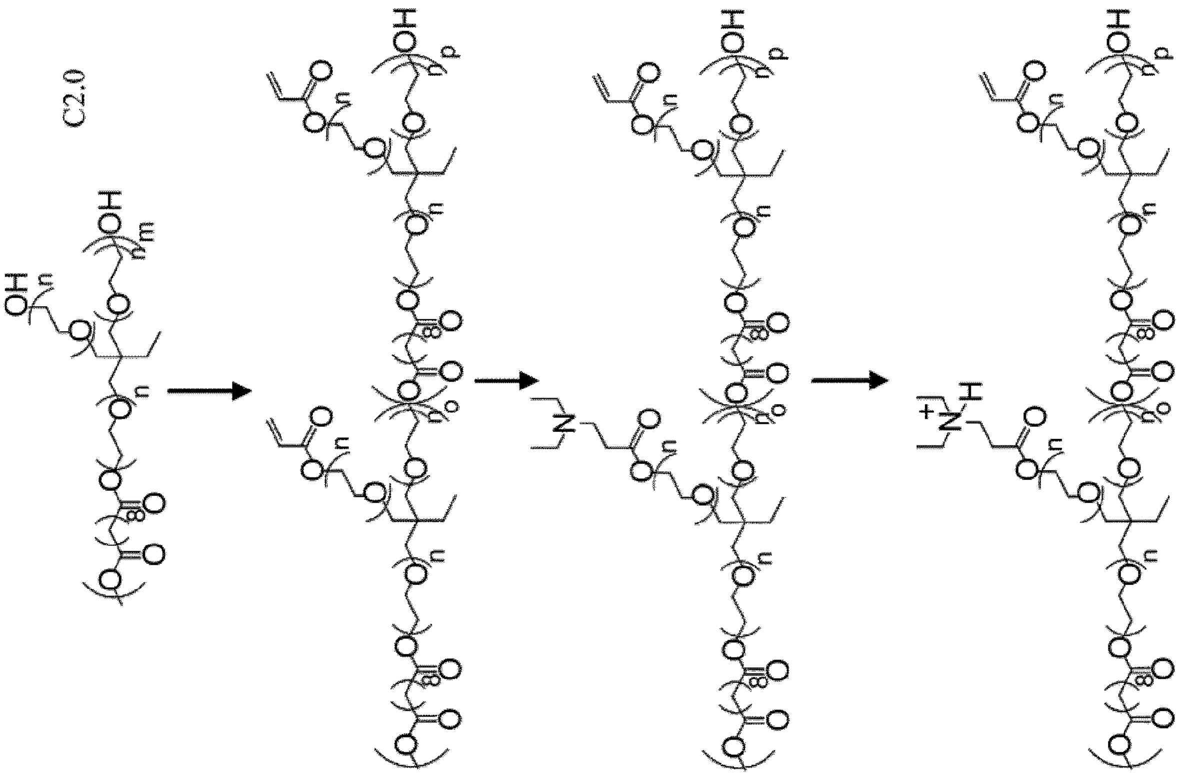
Figure 8:
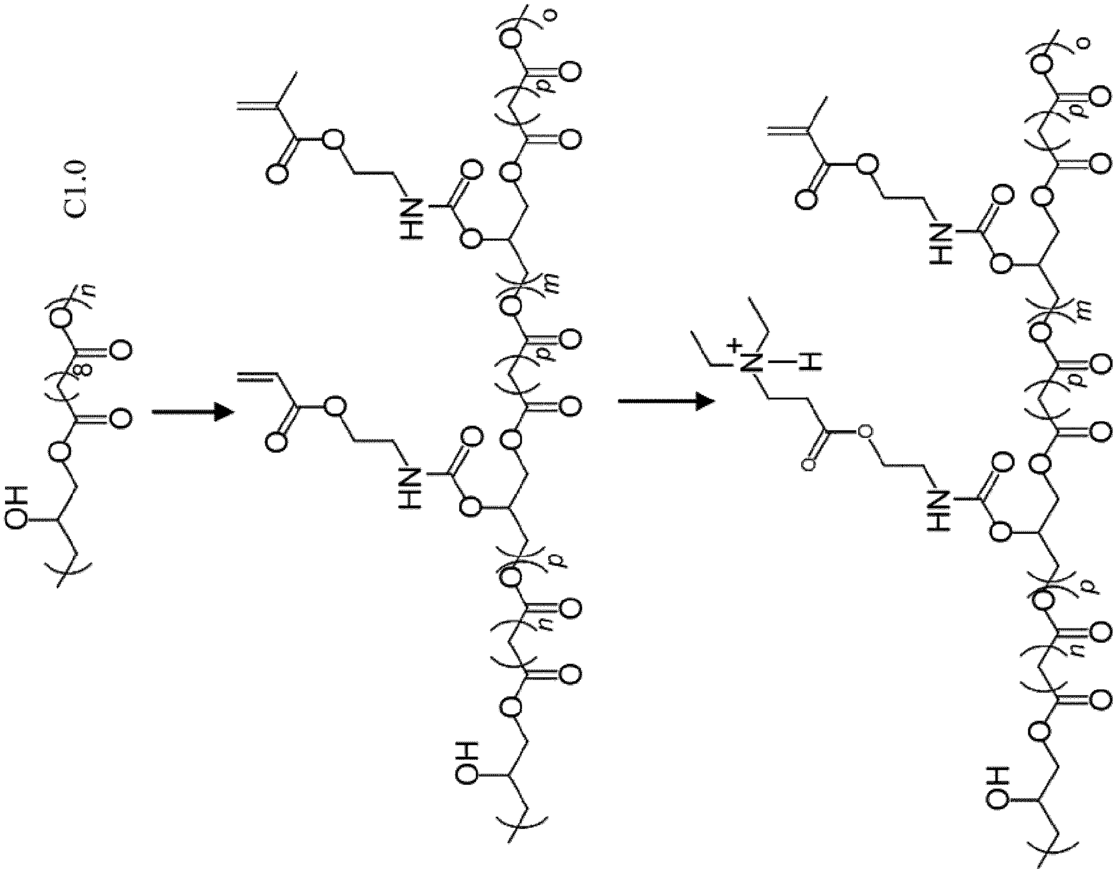

Preferably, the polymeric backbone of the pre-polymer comprises a polymeric unit of the general formula $(\text{-A-B—})_n$, wherein A is derived from a substituted or unsubstituted polyol or mixture thereof and B is derived from a substituted or unsubstituted polyacid or mixture thereof; and n represents an integer greater than 1. The polymeric backbone is made up of repeating monomer units of general formula -A-B—.

The term "substituted" has its usual meaning in chemical nomenclature and is used to describe a chemical compound in which a hydrogen on the primary carbon chain has been replaced with a substituent such as alkyl, aryl, carboxylic acid, ester, amide, amine, urethane, ether, or carbonyl.

Component A of the pre-polymer may be derived from a polyol or mixture thereof, such as a diol, triol, tetraol or greater. Suitable polyols include diols, such as alkane diols, preferably octanediol; triols, such as glycerol, trimethylolpropane, trimethylolpropane ethoxylate, triethanolamine; tetraols, such as erythritol, pentaerythritol; and higher polyols, such as sorbitol. Component A may also be derived from unsaturated polyols, such as tetradeca-2,12-diene-1,14-diol, polybutadiene-diol or other polyols including macromonomer polyols such as, for example polyethylene oxide, polycaprolactone triol and N-methyldiethanoamine (MDEA) can also be used. Preferably, the polyol is substituted or unsubstituted glycerol.

Component B of the pre-polymer is derived from a polyacid or mixture thereof, preferably diacid or triacid. Exemplary acids include, but are not limited to, glutaric acid (5 carbons), adipic acid (6 carbons), pimelic acid (7 carbons), sebacic acid (8 carbons), azelaic acid (nine carbons) and citric acid. Exemplary long chain diacids include diacids having more than 10, more than 15, more than 20, and more than 25 carbon atoms. Non-aliphatic diacids can also be used. For example, versions of the above diacids having one or more double bonds can be used to produce polyol-diacid co-polymers. Preferably the polyacid is substituted or unsubstituted sebacic acid.

Polyol-based polymers described in US 2011/0008277, U.S. Pat. Nos. 7,722,894 and 8,143,042, the contents of which are hereby incorporated by reference, are suitable polymeric backbones for use in the present invention.

Several substituents, such as amines, aldehydes, hydrazides, acrylates and aromatic groups, can be incorporated into the carbon chain. Exemplary aromatic diacids include terephthalic acid and carboxyphenoxy-propane. The diacids can also include substituents. For example, reactive groups like amine and hydroxy can be used to increase the number of sites available for cross-linking. Amino acids and other biomolecules can be used to modify the biological properties. Aromatic groups, aliphatic groups, and halogen atoms can be used to modify the inter-chain interactions within the polymer.

Alternatively, the polymeric backbone of the pre-polymer is a polyamide or polyurethane backbone. For example, polyamine (comprising two or more amino groups) may be used to react with polyacid together with polyol or after reacting with polyol. Exemplary poly(ester amide) includes those described in Cheng et al., Adv. Mater. 2011, 23, 1195-11100, the contents of which are herein incorporated by reference. In other examples, polyisocyanates (comprising two or more isocyanate groups) may be used to react with polyacid together with polyol or after reacting with polyol. Exemplary polyester urethanes include those described in US 2013/231412.

The weight average molecular weight of the pre-polymer (Mw), measured by Gel Permeation Chromatography equipped with a refractive index, may be from about 1,000 Daltons to about 1,000,000 Daltons, preferably from about 2,000 Daltons to about 500,000 Daltons, more preferably from about 2,000 Daltons to about 250,000 Daltons, most preferably from about 2,000 Daltons to about 100,000 Daltons. The weight average molecular weight may be less than about 100,000 Daltons, less than about 75,000 Daltons, less than about 50,000 Daltons, less than about 40,000 Daltons, less than about 30,000 Daltons, or less than about 20,000 Daltons. The weight average molecular weight may be from about 1,000 Daltons to about 10,000 Daltons, from about 2,000 Daltons to about 10,000 Daltons, from about 3000 Daltons to about 10,000 Daltons, from about 5,000 Daltons to about 10,000 Daltons. Preferably, it is about 4,500 Daltons.

The term "about" as used herein means within 10%, preferably within 8%, and more preferably within 5% of a given value or range. According to a specific embodiment, "about X" means X, when X refers to the value or range.

The pre-polymer may have a polydispersity, measured by Gel Permeation Chromatography equipped with a refractive index, below 20.0, more preferably below 10.0, more preferably below 5.0, and even more preferably below 2.5. Preferably, it is about 2.5.

The molar ratios of the polyol to the polyacid in the pre-polymer are suitably in the range of about 0.5:1 to about 1.5:1, preferably in the range of about 0.9:1.1 to about 1.1:0.9 and most preferably about 1:1.

Activated Pre-Polymer

The pre-polymer in the composition of the invention has activated groups on its polymeric backbone.

The activated groups are functional groups that can react or be reacted to form crosslinks. The pre-polymer is activated by reacting one or more functional groups on the monomer units of the backbone to provide one or more functional groups that can react or be reacted to form crosslinks resulting in cured polymer. According to an embodiment, the pre-polymer has activated groups of different nature on its backbone monomeric units. The polymeric backbone of the pre-polymer may comprise a polymeric unit of the general formula $(\text{-A-B—})_n$, wherein A is derived from a substituted or unsubstituted polyol or mixture thereof and B is derived from a substituted or unsubstituted polyacid or mixture thereof.

Suitable functional groups to be activated on the pre-polymer backbone include hydroxy groups, carboxylic acid groups, amines, and combinations thereof, preferably hydroxy and/or carboxylic acid. The free hydroxy or carboxylic acid groups on the pre-polymer can be activated by functionalizing the hydroxy groups with a moiety which can form a crosslink between polymer chains. The groups that are activated can be free hydroxy or carboxylic acid groups on A and/or B moieties in the pre-polymer.

The free hydroxy or carboxylic groups can be functionalized with a variety of functional groups, for example vinyl groups. Vinyl groups can be introduced by a variety of techniques known in the art, such as by vinylation or acrylation. According to the present invention, vinyl groups contain the following structure $—CR_x═CR_yR_z$ wherein $R_x$, $R_y$, $R_z$ are independently from one another, selected from the group consisting of H, alkyl such as methyl or ethyl, aryl such as phenyl, substituted alkyl, substituted aryl, carboxylic acid, ester, amide, amine, urethane, ether, and carbonyl.

Preferably, the activated group is or contains an acrylate group. According to the present invention, acrylate groups may contain the following group: $—C(═O)—CR_p═CR_qR_r$, wherein $R_p$, $R_q$, $R_r$ are independently from one another, selected from the group consisting of H, alkyl such as methyl or ethyl, aryl such as phenyl, substituted alkyl, substituted aryl, carboxylic acid, ester, amide, amine, urethane, ether, and carbonyl. According to an embodiment, the activated pre-polymer contains a mixture of different acrylate groups.

Preferably, all or part of the acrylate groups containing the $—C(═O)—CR_p═CR_qR_r$ group are such that $R_p$, $R_q$ and $R_r$ are H; or such that $R_p$ is $CH_3$, $R_q$ and $R_r$ are H; or such that $R_p$ and $R_q$ are H and $R_r$ is $CH_3$; or such that $R_p$ and $R_q$ are H and $R_r$ is phenyl.

Vinyl groups can also be incorporated in the backbone of the pre-polymer using free carboxyl groups on the pre-polymer. For example, hydroxyethyl methacrylate can be incorporated through the COOH groups of the pre-polymer using carbonyl diimidazole activation chemistry.

In an embodiment of the invention, at least a proportion of the activated groups on the polymeric backbone of the pre-polymer may be alkene groups (e.g. acrylate, methacrylate). The degree of activation (e.g. acrylation) is suitably measured by a technique such as $^1$H NMR. The degree of activation (e.g. acrylation) is suitably characterized as "DA". The proportion of activated groups may be compared to the number of monomer units in the backbone. This can vary and can be from 0.1 to 0.8 mol/mol of monomer unit, preferably from 0.2 to 0.6 mol/mol of monomer unit and most preferably from 0.3 to 0.45 mol/mol of monomer unit, such as 0.3 mol/mol of monomer unit, for achieving optimal robust performance properties at room temperature or elevated temperature up to 40° C., preferably 37° C. It is most preferred when the degree of activation is as described above and the reactive functional group is acrylate i.e. degree of acrylation as above. When the polymeric unit of the backbone is of the general formula $(\text{-A-B—})_n—$, with A derived from a substituted or unsubstituted polyol and B derived from a substituted or unsubstituted polyacid, the monomer unit is of general formula -A-B— and the proportion of activated groups may be quoted per mole of polyacid or per mole of polyol. The DA ranges quoted above are preferably mol/mol of polyacid.

The pre-polymer in the composition of the invention is preferably derived from an activated pre-polymer that has the general formula (I):

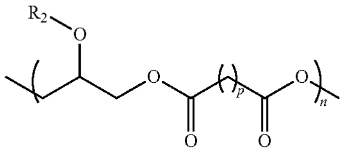

(I)

wherein n and p each independently represent an integer equal to or greater than 1, and wherein $R_2$ in each individual unit represents hydrogen or a polymer chain or $—C(═O)—CR_3═CR_4R_5$, or $C(═O)NR_6—CR_7R_8—CR_9R_{10}—O—C(═O)—CR_3═CR_4R_5$, wherein $R_3$, $R_4$, $R_5$, $R_6$, $R_7$, $R_8$, $R_9$ and $R_{10}$ are independently from one another, selected from the group consisting of H, alkyl such as methyl or ethyl, aryl such as phenyl, substituted alkyl, substituted aryl, carboxylic acid, ester, amide, amine, urethane, ether, and carbonyl.

Preferably, $R_3$, $R_4$ and $R_5$ are H; or $R_3$ is $CH_3$, $R_4$ and $R_5$ are H; or $R_3$ and $R_4$ are H and $R_5$ is $CH_3$; or $R_3$ and $R_4$ are H and $R_5$ is phenyl. Preferably $R_6$, $R_7$, $R_8$, $R_9$ and $R_{10}$ are H.

Preferably, p is an integer from 1-20, more preferably from 2-10, even more preferably from 4-10. It is most preferred when p=8.

Preferably, the pre-polymer in the composition of the invention is derived from an activated pre-polymer containing the monomer unit of the general formula (II):

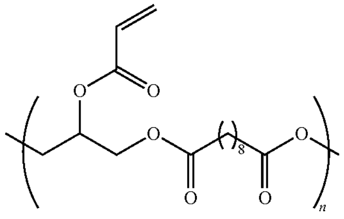

(II)

wherein n represents an integer equal to or greater than 1.

More preferably, the pre-polymer in the composition of the invention is derived from an activated pre-polymer that has a monomer unit of the general formula (II):

(II)

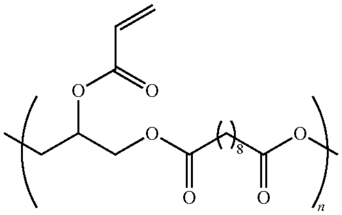

wherein n represents an integer equal to or greater than 1.

In addition to acrylates or other vinyl groups, other agents can be used to provide activated groups on the pre-polymer backbone. Examples of such agents include, but are not limited to, glycidyl, epichlorohydrin, triphenylphosphine, diethyl azodicarboxylate (DEAD), diazirine, divinyladipate, and divinylsebacate with the use of enzymes as catalysts, phosgene-type reagents, di-acid chlorides, bis-anhydrides, bis-halides, metal surfaces, and combinations thereof. Agents may further include isocyanate, aldehyde, epoxy, vinyl ether, thiol, DOPA residues or N-Hydroxysuccinimide functional groups.

Zeta Potential—Activated and Functionalized Pre-Polymer

The present inventors have found that there is a positive correlation between the zeta potential of a composition and the adhesive strength of the composition after curing. The zeta potential of the composition of the invention can vary based on the pre-polymer used, including the pre-polymer's compositional make-up.

"Zeta potential" refers to a charge that develops at the interface between a solid surface and its liquid medium, measured in millivolts (mV) or volts (V). It is an electric potential difference formed between a dispersion medium and stationary layer of fluid attached to a dispersed particle in an interfacial double layer. The magnitude of the zeta potential indicates the degree of electrostatic repulsion between adjacent, similarly charged particles in a dispersion.

The zeta potential of the composition will be affected by the number and the nature of charged atoms in the pre-polymer, but will also be affected by other charged species that may be present in the composition.

Therefore, the pre-polymer of the invention is not only activated by introducing functional groups, preferably acrylate groups, able to form crosslinks, but it is also functionalized with charged atoms.

In a preferred embodiment of the invention, at least a proportion of the activated groups (e.g. acrylate) on the polymeric backbone of the pre-polymer have reacted with a compound containing a charged or chargeable atom, preferably a charged heteroatom, even more preferably a positively charged heteroatom. In the following, they are referred as "activated functionalized groups."

Moreover, at least a proportion of other groups (e.g. hydroxy or carboxylic groups) on the polymeric backbone of the pre-polymer may include a charged heteroatom, preferably a positively charged heteroatom.

The positively charged heteroatom on the pre-polymer may be derived from any element other than carbon or hydrogen. Preferred positively charged heteroatoms are nitrogen, phosphorus and sulfur. Most preferably, the positively charged heteroatom is a positively charged nitrogen atom.

In the composition according to the present invention, the proportion of activated functionalized groups (i.e. activated groups that have been modified such that they contain a charged atom, preferably a charged heteroatom, even more preferably a positively charged heteroatom) compared to the number of monomer units in the backbone can vary depending on the polymer and may suitably range from about 0.05 to about 0.4 mol/mol of monomer unit, preferably from about 0.09 to about 0.25 mol/mol of monomer unit. The proportion of activated functionalized groups is suitably measured by a technique such as $^{1}$H NMR. When the polymeric unit of the backbone is of the general formula (-A-B—)$_n$—with A derived from a substituted or unsubstituted polyol and B derived from a substituted or unsubstituted polyacid, the monomer unit is of general formula -A-B— and the proportion of activated functionalized groups may be quoted per mole of polyacid or per mole of polyol. The ranges quoted above are preferably mol/mol of polyacid. When the functionalized groups, including the activated functionalized groups, on the backbone monomers of the pre-polymer that include a positively charged heteroatom are positively charged nitrogen atoms, then the proportion of functionalized groups that include a positively charged heteroatom is suitably characterized as "DN+". This is the number of positively charged nitrogen atoms compared to the number of monomer units in the backbone. The DN+ parameter is suitably determined using $^{1}$H-NMR spectroscopy, using the characteristic peak of hydrogen atoms located on the positively charged nitrogen atom. The DN+ parameter is suitably quoted as mol/mol of polyacid.

The activated functionalized groups including a positively charged nitrogen atom are preferably of the general formula (III):

(III)

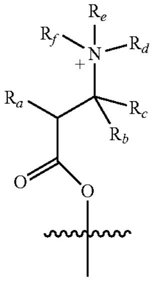

wherein $R_a$, $R_b$, $R_c$, $R_d$, $R_e$ and $R_f$ are independently selected from H, alkyl, alkenyl and aryl. Preferably at least one of $R_d$, $R_e$ and $R_f$ is H.

Alkyl groups for $R_a$, $R_b$, $R_c$, $R_d$, $R_e$ and $R_f$ are suitably selected from the group consisting of straight chain alkyl groups (e.g., methyl, ethyl, propyl, butyl, pentyl, hexyl, heptyl, octyl, nonyl, decyl, etc.) or branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl) or alkyl-substituted cycloalkyl groups. Preferably any alkyl groups are $C_{1-8}$ alkyl groups, more preferably $C_{1-4}$ alkyl groups and most preferably methyl or ethyl groups.

Alkenyl groups for $R_a$, $R_b$, $R_c$, $R_d$, $R_e$ and $R_f$ are suitably selected from the groups consisting of straight-chain alkenyl groups (e.g., ethenyl, propenyl, butenyl, pentenyl, hexenyl, heptenyl, octenyl, nonenyl, decenyl, etc.) or branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. Preferably any alkenyl groups are $C_{2-8}$ alkenyl groups.

Aryl groups for $R_a$, $R_b$, $R_c$, $R_d$, $R_e$ and $R_f$ are suitably selected from the groups consisting of 5- and 6-membered single-ring aromatic groups, as well as multicyclic aryl groups, such as tricyclic or bicyclic (e.g., naphthalene, anthracene, phenanthrene, etc.). Aryl groups can also be fused or bridged with, e.g., alicyclic or heterocyclic rings which are not aromatic so as to form, e.g., a polycycle.

Preferably $R_a$ is hydrogen. Preferably $R_b$ is hydrogen. Preferably $R_c$ is hydrogen.

Preferably one, two or three of $R_d$, $R_e$ and $R_f$ are hydrogen. Most preferably one of $R_d$, $R_e$ and $R_f$ is hydrogen. In another embodiment, $R_d$, $R_e$ and $R_f$ are not hydrogen.

Alternatively, the activated functionalized groups including a positively charged nitrogen atom are preferably of the general formula (IV):

(IV)

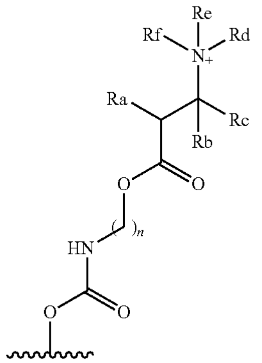

wherein $R_a$, $R_b$, $R_e$, $R_d$, $R_e$ and $R_f$ are as defined above for groups of formula (III), and n represents an integer equal to or greater than 1, preferably from 1 to 4.

According to a preferred embodiment, the activated functionalized group of the general formula (IV) is:

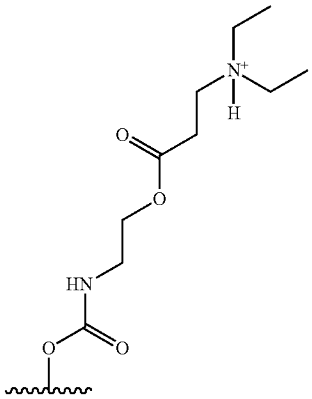

According to another embodiment, the positively charged heteroatoms are phosphorus or sulfur. Example of activated functionalized groups including a positively charged sulfur atom or a positively charged phosphorus atom may be of general formula (V) or (VI):

(V)

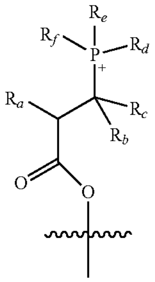

(VI)

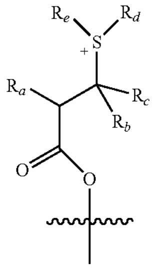

wherein $R_a$, $R_b$, $R_c$, $R_d$, $R_e$ and $R_f$ are as defined above for groups of formula (III).

While in a preferred embodiment, the charged atom of the pre-polymer is present on the activated (e.g. acrylated) groups of the backbone, charged atoms may be present on the backbone as well, for example as substitutions of the polyol group of polyacid, on the hydroxy group of on the carboxylic group.

In one embodiment of the invention, the pre-polymer has the general formula (VII):

(VII)

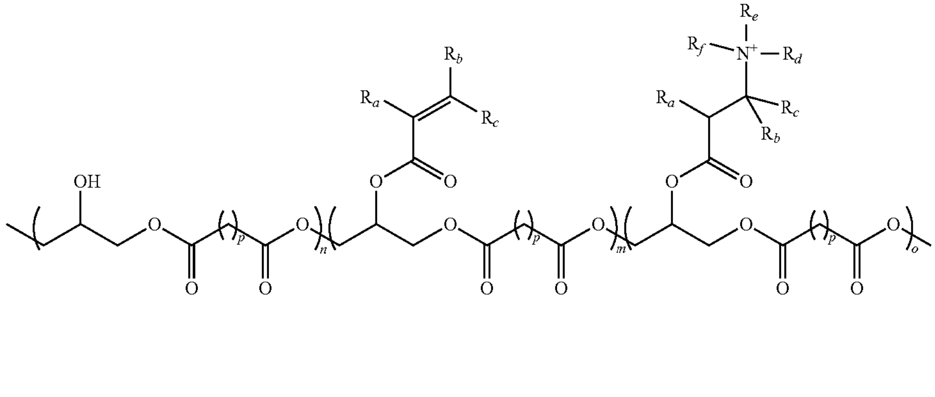

wherein p is between 1 and 20; wherein n, m and o are integers greater than 1, and wherein $R_a$, $R_b$, $R_c$, $R_d$, $R_e$ and $R_f$ are as defined above for groups of formula (III).

p is preferably from 2-10, more preferably from 4-10, and most preferably p=8.

n, m and o are integers greater than 1. The values of n, m and o are suitably sufficiently large that the pre-polymer has a weight average molecular weight as described above, e.g. from about 1,000 Daltons to about 1,000,000 Daltons.

According to the pre-polymer of general formula (VII), some of the hydroxy groups on the backbone monomer units are activated with acrylate groups and some are activated functionalized groups that include charged heteroatom groups including a positively charged nitrogen atom. The preferred ratio of n:m:o will be determined by the preferred amounts of activated groups and activated functionalized groups.

In another embodiment of the invention, the pre-polymer has the general formula (VIII):

(VIII)

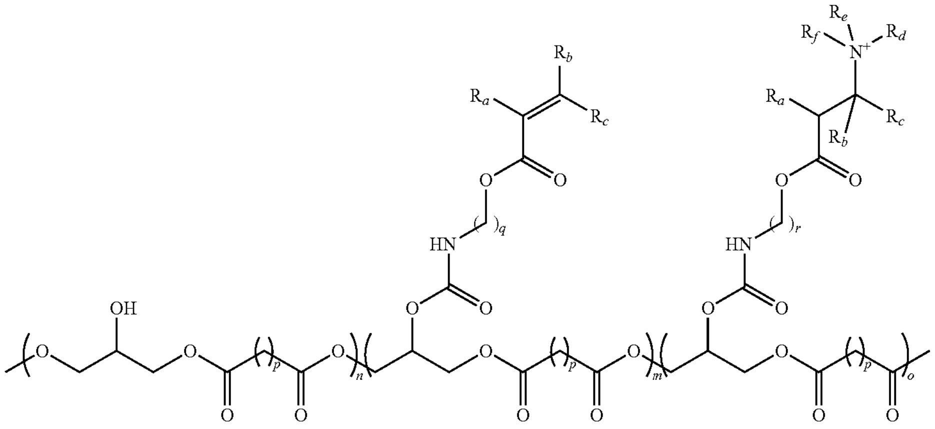

wherein p, q and r are integers between 1 and 20; wherein n, m and o are integers greater than 1, and wherein $R_a$, $R_b$, $R_c$, $R_d$, $R_e$ and $R_f$ are as defined above for groups of formula (III).

p is preferably from 2-10, more preferably from 4-10, and most preferably p=8. q is preferably from 1-4, most preferably q is 2. r is preferably from 1-4, most preferably r is 2.

n, m and o are integers greater than 1. The values of n, m and o are suitably sufficiently large that the pre-polymer has a weight average molecular weight as described above, e.g. from about 1,000 Daltons to about 1,000,000 Daltons.

According to the pre-polymer of general formula (VIII), some of the hydroxy groups on the backbone monomer units are activated with acrylate groups and some are activated functionalized groups that include charged heteroatom groups including a positively charged nitrogen atom. The preferred ratio of n:m:o will be determined by the preferred amounts of activated groups and activated functionalized groups.

Zeta Potential Measurement

For the compositions of the present invention, the zeta potential can be measured using the following protocol:

The instrument used to measure the zeta potential is a Zetasizer Nano-ZS Zen 3600. Zeta potential cells DTS1070 from Malvern are used.

A standard solution is prepared by weighing 15 mg of the pre-polymer into a glass vial. 50 µL of isopropanol and 1 mL of deionized water are added. The solution is submitted to a vortex to achieve complete dissolution of the pre-polymer. 50 µL of the resulting solution is transferred to a 20 mL glass vial and 5 mL of deionized water is added.

1 mL of the solution is added to the zeta potential cell and the cell is placed in the Zetasizer instrument. The instrument is set to "Manual" and then "measurement type—Zeta potential sample" with the following choices: Material—polystyrene latex, Dispersant—water, General options—Smoluchowski model, Temperature—37° C., Equilibration time—120 s, Cell—disposable folded capillary cells.

Three measurements are taken with the automatic mode with a minimum of 10 runs and a maximum of 100 runs. 3 measurements are run per sample with zero delay between measurements.

In the composition according to the present invention, the zeta potential (as measured according to the protocol described above) is between 0 and about 45 mV, preferably between about 5 and about 40 mV, more preferably between about 5 and about 30 mV.

Composition

The composition according to the present invention can be manufactured in the presence and/or mixed with a coloring agent. Preferred examples of coloring agents are the ones recommended by the FDA for use in medical devices, pharmaceutical products or cosmetics.

Similarly, the composition can further comprise stabilizers, for example MEHQ or N-Phenyl-2-naphthylamine (PBN).

The activated and functionalized pre-polymer of the composition can be further reacted with one or more additional materials to modify the crosslinks between the polymer chains. For example, prior to or during curing/crosslinking, one or more hydrogel or other oligomeric or monomeric or polymeric precursors (e.g., precursors that may be modified to contain acrylate groups) such as poly(ethylene glycol), dextran, chitosan, hyaluronic acid, alginate, other acrylate based precursors including, for example, acrylic acid, butyl acrylate, 2-ethylhexyl acrylate, methyl acrylate, ethyl acrylate, acrylonitrile, n-butanol, methyl methacrylate, acrylic anhydride, metahcrylic anhydride and TMPTA, trimethylol propane trimethacrylate, pentaerythritol trimethacrylate, pentaerythritol tetramethacrylate, ethylene glycol dimethacrylate. dipentaerythritol penta acrylate, Bis-GMA (Bis phenol A glycidal methacrylate) and TEGDMA (tri-ethylene, glycol dimethacrylate), sucrose acrylate; other thiol based precursors (monomeric or polymeric); other epoxy based precursors; and combinations thereof, can be reacted with the acrylated pre-polymer.

The composition according to the present invention can be a surgical composition and is suitably used as a tissue sealant and/or adhesive. The composition suitably has flow characteristics such that it can be applied to the desired area through a syringe or catheter but is sufficiently viscous to remain in place at the site of application without being washed away by bodily fluids, such as water and/or blood.

Preferably, the viscosity of the composition is 500 to 100,000 cP, more preferably 1,000 to 50,000 cP, even more preferably 2,000 to 40,000 cP and most preferably 2,500 to 25,000 cP. Viscosity analysis is performed using a Brookfield DV-II+Pro viscosimeter with a 2.2 mL chamber and SC4-14 spindle, the speed during the analysis is varied from 5 to 80 rpm. The above-mentioned viscosity is present in the relevant temperature range for medical application i.e. room temperature up to 40° C., preferably 37° C.

The composition of the invention may be incubated in bodily fluids, such as blood, prior to administration and curing, without a substantial decrease in adhesive strength when cured.

The composition of the invention is suitably stable in bodily fluids, such as blood. More particularly, the composition of the invention suitably does not spontaneously crosslink in bodily fluids absent the presence of an intentionally applied stimulus such as light, for example UV light, heat, or chemical initiator to initiate crosslinking.

The composition can be cured using a free radical initiated reaction, such as, for example, by photo-initiated polymerization, thermally-initiated polymerization, and redox initiated polymerization.

Preferably, the composition is irradiated with light, for example ultraviolet (UV) light in the presence of a photoinitiator to facilitate the reaction. Examples of suitable photoinitiators include, but are not limited to: 2-dimethoxy-2-phenyl-acetophenone, 2-hydroxy-1-[4-(hydroxyethoxy) phenyl]-2-methyl-1-propanone (Irgacure 2959), 1-hydroxycyclohexyl-1-phenyl ketone (Irgacure 184), 2-hydroxy-2-methyl-1-phenyl-1-propanone (Darocur 1173), 2-benzyl-2-(dimehylamino)-1-[4-morpholinyl) phenyl]-1-butanone (Irgacure 369), methylbenzoylformate (Darocur MBF), oxy-phenyl-acetic acid-2-[2-oxo-2-phenyl-acetoxy-ethoxy]-ethyl ester (Irgacure 754), 2-methyl-1-[4-(methylthio)phenyl]-2-(4-morpholinyl)-1-propanone (Irgacure 907), diphenyl(2,4,6-trimethylbenzoyl)-phosphine oxide (Darocur TPO), phosphine oxide, phenyl bis(2,4,6-trimethyl benzoyl) (Irgacure 819), and combinations thereof.

Preferably, the composition is irradiated with visible light (typically blue light or green light) in the presence of a photoinitiator to facilitate the reaction. Examples of photoinitiators for visible light include, but are not limited to, diphenyl(2,4,6-trimethylbenzoyl)-phosphine oxide, eosin Y disodium salt, N-Vinyl-2-Pyrrolidone (NVP) and triethanolamine, and camphorquinone.

In applications of the composition involving in vivo photopolymerization and other medical applications, the use of cytocompatible photoinitiators is preferred and may be required by regulatory agencies. Photoinitiator Irgacure 2959 may be used, which causes minimal cytotoxicity (cell death) over a broad range of mammalian cell types and species.

In order for the photopolymerization to occur, the composition (and the substrate to which the composition is applied, if applicable) is preferably sufficiently transparent to the light.

In applications when the composition is cured in vivo, the temperature at which curing occurs is preferably controlled as not damage the tissue on which the composition has been applied. Preferably, the composition is not heated above 45° C. during irradiation, more preferably not above 37° C., and even more preferably not above 25° C.

In addition to photochemical crosslinking, the composition can be cured thermally, by Mitsunobu-type reaction, by redox-pair initiated polymerization for example benzoyl peroxide, N,N-dimethyl-p-toluidine, ammonium persulfate, or tetramethylenediamine (TEMED), and by a Michael-type addition reaction using a bifunctional sulfhydryl compound.

In one embodiment, a redox composition (i.e. a composition that can be cured thermally by redox-pair initiated radical polymerization) may comprise 0.1 to 5 wt % of a reducing agent, e.g., 4-N,N Trimethylaniline, N,N-Bis(2-hydroxyethyl)-p-toluidine, N,N-Dimethylaniline, N,N-Diethylaniline, sodium p-toluenesulfonate or N-Methyl-N-(2-hydroxyethyl)-p-toluidine; 0 to 5 wt % of an oxygen inhibitor, e.g., 4-(Diphenylphosphino)styrene or triphenylphosphine; 0.005 to 0.5 wt % of a working time agent, e.g., Tempol or 4-methoxyphenol; and 0.1 to 10 wt % of an oxidant, e.g., ammonium persulfate, potassium persulfate or benzoyl peroxide. The reaction onset of the redox-pair initiated polymerization is affected by the absolute and relative amounts of the different reagents.

Upon polymerization, the activated and functionalized pre-polymer forms a crosslinked network with improved adhesive properties and exhibits significant adhesive strength even in the presence of blood and other bodily fluids. The cured polymer obtained after curing is preferably sufficiently elastic to resist movement of the underlying tissue, for example contractions of the heart and blood vessels. The adhesive can provide a seal, preventing the leakage of fluids or gas. The adhesive is preferably biodegradable and biocompatible, causing minimal inflammatory response. The adhesive is preferably elastomeric.

Biodegradability can be evaluated in vitro, such as in phosphate buffered saline (PBS) or in acidic or alkaline conditions. Biodegradability can also be evaluated in vivo, such as in an animal, for example mice, rats, dogs, pigs or humans. The rate of degradation can be evaluated by measuring the loss of mass of the polymer over time in vitro or in vivo.

The cured composition, alone or coated on a patch or tissue suitably exhibits a 90° pull off adhesive strength of at least 0.5 $N/cm^2$, preferably at least 1 $N/cm^2$ and even more preferably at least 2 $N/cm^2$, for example 1.5 $N/cm^2$ to 2 $N/cm^2$, but preferably greater than 5 $N/cm^2$, for example up to 6 $N/cm^2$ or 7 $N/cm^2$ or greater. Pull off adhesive strength refers to the adhesion value obtained by attaching an adhesive article or sample to wet tissue, such as epicardial surface of cardiac tissue or blood vessels immobilized on a flat substrate, such as a metallic stub. The 90° pull off adhesion test determines the greatest perpendicular force (in tension) that a surface area can bear before adhesive detachment (N. Lang et al., Sci. Transl. Med., 2014, 6, 218ra6).

According to preferred embodiment, the composition of the invention is cured in light and in presence of a photo initiator and the cured composition exhibits a 90° pull off adhesive strength of at least 0.5 $N/cm^2$, preferably at least 1 $N/cm^2$ and even more preferably at least 2 $N/cm^2$, for example 1.5 N/$cm^2$ to 2 N/$cm^2$, but preferably greater than 5 N/$cm^2$, for example up to 6 N/$cm^2$ or 7 N/$cm^2$ or greater.

The cured composition can desirably also exhibit a burst pressure of greater than 100 mmHg, preferably in the range of 400 mmHg to 600 mmHg or greater, for example 400 mmHg or 500 mmHg. Burst pressure or strength refers to the pressure value obtained to burst an explanted porcine carotid arterial vessel, which has an incision coated with the composition.

The composition of the present invention when cured in light and in the presence of a photo-initiator preferably has one or more of the following properties:

i) 90° pull off strength greater than 0.5 N/$cm^2$, preferably 2 to 7 N/$cm^2$ or greater; and ii) burst performance of greater than 100 mmHg, preferably 200 to 300 mmHg or greater.

According to preferred embodiment, the composition of the invention is used as adhesive, i.e., is able after curing to bind strongly to a surface or to bind one surface to another.

According to an alternative embodiment, the composition of the invention is used as sealant, i.e., it is able after curing to prevent leaking (e.g., of fluid or gas) by forming a barrier or filling a void volume.

Besides adhesion and sealing of wet biological tissue, the composition may adhere to and seal a variety of hydrophilic or hydrophobic substrates, natural or synthetic, including polyethylene terephthalate, expanded polyethylene terephthalate, polyester, polypropylene, silicones, polyurethanes, acrylics, fixed tissue (e.g., pericardium), ceramics or any combinations thereof.

Method of Preparation

The method for preparing the composition of the present invention, comprises several required steps, which may accommodate several variations. According to a preferred embodiment, said method comprises the steps of:

i) polymerization of monomers to provide the pre-polymer backbone;
ii) activation of the backbone monomer units to provide the activated pre-polymer; and
iii) functionalization of the activated pre-polymer with a compound containing a charged or chargeable atom to provide the activated and functionalized pre-polymer.

The monomers are preferably component A (polyol or a mixture of polyols) and component B (polyacid or a mixture of polyacids) and are suitably added together in a molar ratio range of 0.5:1 to 1.5:1, preferably 0.9:1.1 and most preferably 1:1. Where component A is glycerol and component B is sebacic acid and added in a 1:1 molar ratio, there are three hydroxy groups on glycerol for two carboxyl groups on the sebacic acid. Therefore, an extra hydroxy group on glycerol is available for activation, as well as terminal carboxylic acid groups.

The conditions for step i) may include a temperature range of 100 to 140° C., preferably 120 to 130° C., an inert atmosphere, preferably comprising nitrogen, and under vacuum.

In a preferred embodiment, hydroxy or carboxylic groups are present on the pre-polymer backbone obtained following step i).

The activation in step ii) is suitably achieved by acrylation of the pre-polymer backbone.

In a preferred embodiment, the activation is done through acrylation of the hydroxy or carboxylic groups. The carboxylic activation may result in the formation of anhydride that can be eliminated (totally or partially), for example using ethanol (see for example WO2016/202984).

One or more acrylates may be used as the acrylating agent. The acrylate may contain the following group: $-C(=O)-CR_p=CR_qR_r$, wherein $R_p$, $R_q$, $R_r$ are independently from one another, selected from the group consisting of H, alkyl such as methyl or ethyl, aryl such as phenyl, substituted alkyl, substituted aryl, carboxylic acid, ester, amide, amine, urethane, ether, and carbonyl. Preferably $R_p$ is H. Most preferably the acrylating agent is acryloyl chloride.

Step ii) can be carried out in the presence of one or more solvents or catalysts, examples including dichloromethane (DCM), ethyl acetate (EtOAc) dimethylaminopyridine (DMAP), and triethylamine (TEA) or any combination thereof.

Several purifications steps may be performed at this stage, preferably water washings steps, from 2 to 11 times, preferably 2 to 8 times, most preferably 8 times.

Alternatively, activation in step ii) can be acrylation using an isocyanate acrylate compound. A preferred isocyanate acrylate compound is 2-isocyanatoethyl(meth)acrylate.

For the functionalization step iii), in a preferred embodiment, an amine moiety is grafted to the pre-polymer backbone followed by acidification to form the charged amine.

The grafting of the amine can be performed through specific substitutions of the activated pre-polymer, on the hydroxy, carboxylic, or activated (e.g. acrylate) groups.

According to preferred embodiment, the acrylate groups are reacted with an amine to give a grafted tertiary amine group, and the resulting amine is acidified to give an ammonium group (see C1.3 in Examples).

According to another embodiment, the amine is, alternatively or additionally, grafted on the carboxylic acid after being modified to an acid anhydride during the activation step (see C1.5 in Examples). In such case, amide is formed.

According to another embodiment, the amine is, alternatively or additionally, grafted on the carboxylic acid modified (e.g. by being modified to acid anhydride) to react more easily with nucleophiles, such as any bi-functional molecules bearing an alcohol and an amine group, more preferably diethylethanolamine (see C1.6 in Examples).

According to the invention, the amine may be a primary amine, a secondary amine or a tertiary amine. Preferred amines include diethylamine.

The amination step iii) is preferably carried out in a solvent, such as dichloromethane.

Charging of the amine may be carried out through acidification. Acidification is suitably carried out in the presence of an acid, such as a carboxylic acid, examples including formic acid and acetic acid, or hydrochloric acid.

According to a specific embodiment, the activation step ii) and functionalization step iii) may occur in the same reaction step, without the need of acidification.

At least one additive may be added to the composition obtained at step iii). In a preferred embodiment, said additive is selected from the group consisting of photoinitiators, radical inhibitors, and dyes.

According to a preferred embodiment, the method further comprises one or more purification steps iv) to ensure that solvents, by-products, impurities, or un-reacted products are removed from the composition. These may be conducted throughout any reaction steps and more than one purification technique may be applied during the preparation of the composition.

In a preferred embodiment, such purification steps may include washes in aqueous media. Phase separation during water washings can be improved by the use of salts solubilized in the aqueous phase (e.g. from about 50 to about 500 g/L salt aqueous solution, preferably about 300 g/L salt, for example sodium chloride, aqueous solution). According to a preferred embodiment, the water washing is salted water washing. Examples of salts include, but are not limited to, sodium chloride or potassium chloride.

According to a preferred embodiment, such purification steps may be conducted either by solvent evaporation or supercritical carbon dioxide extraction.

Uses

Tissue Adhesion and Sealing

The composition according to the invention may be used for adhering or sealing targeted surfaces including tissue, graft material such as PTFE-based graft, or any combination thereof. The method for adhering or sealing targeted surfaces comprises applying the composition to the surface and curing the composition.

Unlike conventional tissue adhesives that spontaneously activate during application or in the presence of water, or adhesives that are hydrophilic and thus are subject to washout prior to curing, the composition according to the invention can be applied to wet substrates without activation or displacement. The composition can also be applied to dry substrates.

The composition may also be used for adhering tissue to the surface of a medical device. The composition can be used in medical devices, either as part or all of a device or to adhere a device to tissue. The method for adhering tissue to the surface of a medical device comprises applying the composition to the surface of the tissue and/or medical device and curing the composition. The composition can also be used to join tissue, including one or more tissue in vivo.

Surgical adhesives comprising the composition according to the invention can also be used for other applications. Examples of applications include to stop bleeding, for example, due to a wound or trauma, during surgery such as after suturing a graft to a vessel, or after vascular access in endovascular procedures. The adhesive does not need to be removed before the surgeon sutures the wound closed since it will degrade over time. Other types of wounds that can be treated include, but are not limited to, wounds that leak, wounds that are hard to close or that fail to heal properly through normal physiologic mechanisms. The application can be performed both inside or outside the body, for human or veterinary use.

The composition according to the invention can also be fabricated into a biodegradable stent. The stent can increase the diameter of a blood vessel to increase flow through the vessel, but since the stent is biodegradable, the blood vessel can increase in diameter with a reduced risk of thrombosis or covering the stent with scar tissue, which can re-narrow the blood vessel. The composition can cover an outer surface of a stent to help adhere the stent to a vessel wall in a manner that is less damaging to the tissue than an uncovered stent or avoid its displacement inside the body. Similarly, the composition can cover the surface of any devices which are in contact with tissue to provide a suitable interface that can be adhesive to tissue.

The composition according to the present invention can be used in a variety of other applications where an adhesive or sealant is required. These include, but are not limited to, air leaks following a lung resection; to reduce the time for surgical procedures; to seal dura; to ease laparoscopic procedures; as a degradable skin adhesive; as a hernia matrix to prevent or to reduce the need for stables or tacks; to prevent blood loss; to manipulate organs or tissues during surgical procedures; to secure corneal transplants in place; to patch a heart to deliver drugs and/or to reduce dilation of the heart after myocardial infarction; to attach another material to a tissue; to augment sutures or staples; to distribute forces across tissue; to prevent leaks; as a barrier membrane on the skin to prevent evaporation of water from burnt skin; as a patch for delivery of anti-scar or antimicrobial medication; to attach devices to tissue; to attach devices to mucus membrane as a tape to secure devices within an oral cavity, such as to hold dentures and oral appliances; as a tape to anchor soft tissue to bone; to prevent the formation of holes in tissue; and to enhance/augment mechanical properties of tissues, etc.

Delivery of Bioactive Molecules

The composition according to the invention described may also contain one or more pharmaceutical, therapeutic, prophylactic, and/or diagnostic agents that are released during the time period that the material functions as a sealant/adhesive. The agent may be a small molecule agent, for example, having molecular weight less than 2000, 1500, 1000, 750, or 500 Daltons, a biomolecule, for example peptide, protein, enzyme, nucleic acid, polysaccharide, growth factors, cell adhesion sequences, such as RGD sequences or integrins, extracellular matrix components, or combinations thereof. Exemplary classes of small molecule agents include, but are not limited to, anti-inflammatories, analgesics, antimicrobial agents, and combinations thereof. Exemplary growth factors include, without limitation, TGF-β, acidic fibroblast growth factor, basic fibroblast growth factor, epidermal growth factor, IGF-I and II, vascular endothelial-derived growth factor, bone morphogenetic proteins, platelet-derived growth factor, heparin-binding growth factor, hematopoetic growth factor, peptide growth factor, or nucleic acids. Exemplary extracellular matrix components include, but are not limited to, collagen, fibronectin, laminin, elastin and combinations thereof. Proteoglycans and glycosaminoglycans can also be covalently or non-covalently associated with the composition of the present invention.

Tissue Support

The composition according to the invention can be used to create tissue supports by forming shaped articles within the body to serve a mechanical function. The shaped articles may be produced by a variety of fabrication techniques known in the art, including 3D printing. Such articles may exert functions, such as holding two tissues together or positioning the tissue in a specific position inside or outside the body.

The tissue can be coated with a layer of the materials, for example, the lumen of a tissue, such as a blood vessel to prevent restenosis, reclosure or vasospasm after vascular intervention.

The composition may also contain one or more types of cells, such as connective tissue cells, organ cells, muscle cells, nerve cells, and combinations thereof. Optionally, the material is seeded with one or more of tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, and bone-forming cells. The combination of cells with the material may be used to support tissue repair and regeneration.

Anti-Adhesion Barriers

The composition according to the invention herein described can be applied to reduce or prevent the formation of adhesions after surgical procedures. For example, the composition can be applied to prevent adhesion of brain tissue to the skull after brain surgery or implantation of devices to prevent peritoneal adhesion.

Other Applications

The compositions can also be used to coat tools, such as surgical instruments, for example, forceps or retractors, to enhance the ability of the tools to manipulate objects. The compositions can also be used in industrial applications where it is useful to have a degradable adhesive that is biocompatible, for example, to reduce potential toxicity of the degradation products, such as marine applications, for example, in underwater use or attaching to the surface of boats. The compositions can be also used to produce shaped objects by a variety of techniques known in the art, including 3D printing. The shaped object may have micro or nanoscale resolution.

The present invention will now be illustrated, but in no way limited, by reference to the following examples.

EXAMPLES

Example 1: Acrylate Functionalization (C1.4)

(i) Synthesis of Poly(Glycerol Sebacate) (PGS, C1.0):

1. Equimolar amounts of glycerol and sebacic acid were weighed.
2. The reaction mixture temperature set between 120 and 130° C. until the monomers were completely melted.
3. Upon melting of the reagents, the bath or reaction temperature was reduced to the target value of 120° C. and stirring started.
4. The air inside the flask was replaced with nitrogen using three vacuum/purging cycles.
5. The reaction was followed for 8 hours.
6. The nitrogen supply was then removed, and the pressure reduced using a vacuum pump set to a target of 15 mBars.

The reaction was followed until the targeted Mw (about 3,000 Da) and polydispersity (<3) were achieved. The glycerol: sebacic acid molar ratio targeted was 1:1, as confirmed by nuclear magnetic resonance (NMR).

(ii)/(iii): Activation (Acrylation) and Functionalization (Amination Followed by Acidification) of PGS:

The following procedure was used to activate hydroxy groups on the PGS backbone:

The PGS (C1.0) was reacted with acryloyl chloride (~0.37 g of acryloyl chloride (AcCl) per 1 gram of PGS) in 10% (w/v) dichloromethane (DCM) and triethylamine (~0.4 g of triethylamine (TEA) per 1 gram of PGS). Ethanol capping of the acrylated PGS (C1.1) was achieved by reaction with ethanol, overnight, at a temperature in the range of between 30 and 50° C.

The resulting pre-polymer is purified by water washings, preferably 8 times, and was distilled to pre-polymer poly (glycerol sebacate)acrylate, PGSA (C1.2).

The acrylated PGS was reacted with diethylamine (61 mg of diethylamine (DEA) per 1 gram of acrylated PGS) in dichloromethane at 40° C. for 5 hours, thereby providing aminated and acrylated PGS (pre-polymer C1.3).

The aminated and acrylated PGS was acidified with acetic acid at room temperature for 15 minutes. The product was purified by brine washing and distillation. The organic solution was then concentrated to 50% (w/w). Additives were added (Irgacure TPO photoinitiator, and radical inhibitor MEHQ), and the product was purified by $scCO_2$ extraction.

The proportion of groups that include a positively charged nitrogen atom (DN+) and the proportion of groups that include an acrylate group (DA) were measured using $^1H$ NMR spectroscopy. The DN+ was 0.18 mol/mol of polyacid and the DA was 0.31 mol/mol of polyacid. This final composition, comprising pre-polymer C1.4, is a composition according to the invention.

Example 2: Acrylate Functionalization (C1.4)

Synthesis of PGS (C1.0)

Synthesis of PGS was done as presented in Example 1.

Activation and Functionalization of PGS—Acrylation, Amination and Acidification

The following procedure was used to activate hydroxy groups on the PGS backbone:

The PGS was reacted with acryloyl chloride (0.37 g of AcCl per g of PGS) in 10% (w/v) dichloromethane and triethylamine (0.4 g of TEA per 1 g of PGS), thereby providing acrylated PGS. Ethanol capping of the acrylated PGS was achieved by reaction with ethanol, overnight, at a temperature in the range of between 30 and 50° C. The resulting pre-polymer (C1.2) was purified by two water washings.

The acrylated PGS was reacted with diethylamine (around 100 mg of DEA per g of PGS) in dichloromethane at 40° C. for 5 hours, thereby providing aminated PGSA (C1.3).

The aminated PGSA was acidified with acetic acid (2 molar equivalents compared to DEA) at room temperature for 15 minutes. The product was purified by brine washings and distillation. The proportion of groups that include a positively charged nitrogen atom (DN+) and the proportion of groups that include an acrylate group (DA) were measured using $^1H$ NMR spectroscopy. The DN+ was 0.21 mol/mol of polyacid and the DA was 0.38 mol/mol of polyacid.

Additives were added (Irgacure TPO photoinitiator, and radical inhibitor MEHQ), and the product, C1.4, was purified by $scCO_2$ extraction. The final DN+ was 0.21 mol/mol of polyacid and the final DA was 0.29 mol/mol of polyacid (composition according to the invention comprising pre-polymer C1.4).

Example 3: Acrylate Functionalization and Simultaneous Anhydride Removal (C1.5)

Synthesis of PGS (C1.0)

Synthesis of PGS was done as presented in Example 1.

Activation and Functionalization of PGS—Acrylation, Amination and Acidification

The following procedure was used to activate hydroxy groups on the PGS backbone:

The PGS was reacted with acryloyl chloride (0.37 g of AcCl per g of PGS) in 10% (w/v) dichloromethane and triethylamine (0.4 g of TEA per g of PGS), thereby providing acrylated PGS.

Diethylamine (around 170 mg of DEA per g of PGS), substitutes ethanol capping and is directly added to the previous solution and left under stirring for 20 h at RT, thereby providing aminated PGSA and anhydride removal in one step.

The aminated PGS was acidified with acetic acid at room temperature for 15 minutes (2 molar equivalents of acetic acid compared to DEA). The product was purified by brine washings and distillation. The proportion of groups that include a positively charged nitrogen atom (DN+) and the proportion of groups that include an acrylate group (DA) were measured using 41 NMR spectroscopy. The DN+ was 0.54 mol/mol of polyacid and the DA was 0.20 mol/mol of polyacid. Additives were added (Irgacure TPO photoinitiator, and radical inhibitor MEHQ), and the product was purified by $scCO_2$ extraction. The final DN+ was 0.20 mol/mol of polyacid and the final DA was 0.39 mol/mol of polyacid (composition according to the invention comprising pre-polymer C1.5).

Example 4: Pre-Polymer Functionalization Through Anhydride Removal (C1.6)

Synthesis of PGS (C1.0)

Synthesis of PGS was done as presented in Example 1.

Activation and Functionalization of PGS—Acrylation, Modification with N,N-Diethylethanolamine, Acidification The following procedure was used to activate hydroxy groups on the PGS backbone:

The PGS (C1.0) was reacted with acryloyl chloride (~0.37 g of acryloyl chloride (AcCl) per 1 gram of PGS) in 10% (w/v) dichloromethane (DCM) and triethylamine (~0.4 g of triethylamine (TEA) per 1 gram of PGS), thereby providing acrylated PGS (C1.1).

Functionalization of the activated pre-polymer was performed by modifying the generated acid anhydrides with N,N-Diethylethanolamine.

N,N-Diethylethanolamine (82 mL) was added to 450 mL of the acrylated PGS (C1.1). The mixture was heated to 40° C. for 24 h. Then the mixture was purified by brine washing and the organic layer was dried and concentrated to 50% (w/w) solution. Then, acetic acid (70 mL) was added and the mixture was stirred for 5 min. The organic layer was washed with brine, dried and concentrated to 50% (w/w) solution. Additives were added (Irgacure TPO photoinitiator) and batch was purified by solvent evaporation and adhesion performance assessed. The DA was 0.74 mol/mol of polyacid, and the final DN+ was not possible to be determined for the composition according to the invention comprising C1.6.

Example 5: Pre-Polymer Activation Alternative (C1.9 and C.10)

Synthesis of PGS (C1.0)

Synthesis of poly(glycerol sebacate) was as described in Example 1.

Activation (Acrylation) and Functionalization (Amination Followed by Acidification) of PGS The following procedure was used to activate hydroxy groups on the PGS backbone:

The PGS (C1.0) was reacted with isocyanate acrylate (~0.306 g of isocyanate acrylate per 1 gram of PGS) in 20% (w/v) ethyl acetate, thereby providing acrylated PGS (pre-polymer C1.9).

The resulting activated pre-polymer was functionalized with no intermediate purification steps, by reacting with diethylamine (60 mg of diethylamine per 1 gram of activated PGS) in ethyl acetate at 55° C. for 5 hours. The functionalized and activated PGS was acidified with acetic acid (0.670 mL AcOH per 1 gram of C1.9 was added) at room temperature for 15 minutes. The product (C1.10) was purified by brine washing and distillation. The organic solution was then concentrated to 50% (w/w). Additives were added (Irgacure TPO photoinitiator, and radical inhibitor MEHQ), and the product was purified by $scCO_2$ extraction.

The proportion of groups that include a positively charged nitrogen atom (DN+) and the proportion of groups that include an acrylate group (DA) were measured using $^1H$ NMR spectroscopy. The DN+ was 0.19 mol/mol of polyacid, and the DA was 0.30 mol/mol of polyacid. This final product comprising pre-polymer C1.10 is a composition according to the invention.

Example 6: Simultaneous Activation and Functionalization (C1.7 and C1.8)

Synthesis of PGS (C1.0) Synthesis of PGS was done as presented in Example 1.

Simultaneous Activation and Functionalization of PGS—Simultaneous Acrylation and Amination PGS is dissolved in DCM and a base (YEA or DIPEA) is added (1.20 mol of base per 1 mol of glycerol). In a second vial, AcCl is dissolved in DCM (1.15 mol of AcCl per 1 mol of glycerol). Both vials are flushed 3 times with vacuum/nitrogen cycles. Vial containing the AcCl solution is cooled down to 0° C. and protected from light. The PGS+base solution is added dropwise into the AcCl solution over approximately 3 hours.

The solution is then left to come back to room temperature and left under stirring for 1 hour.

Solution is washed once with salted water, dried with magnesium sulfate and filtered.

Ethanol capping of the acrylated PGS was achieved by reaction with ethanol, overnight, at a temperature in the range of between 30 and 50° C.

Additives were added (Irgacure TPO photoinitiator, and radical inhibitor MEHQ), and the product was purified by $scCO_2$ extraction. Composition C1.7 preferentially uses base triethylamine (TEA). Composition C1.8 preferentially uses base N,N-diisopropylethylamine (DIPEA).

Example 7: Aminated Poly (Trimethylolpropane Ethoxylate-Co Sebacate) Acrylate (Pre-Polymer C2.1)

Synthesis of Poly (Trimethylolpropane Ethoxylate-Co Sebacate) (PTS, Pre-Polymer C2.0)

PTS is a polymer analogous to PGS except that instead of being prepared from sebacic acid and glycerol it is prepared from sebacic acid and trimethylolpropane ethoxylate.

The following general protocol was initially applied to synthesize poly (trimethylolpropane ethoxylate-co-sebacate) (PTS, pre-polymer C2.0):

1. Equimolar amounts of trimethylolpropane ethoxylate and sebacic acid were weighed.
2. The reaction mixture temperature set between 120 and 130° C. until the monomers were completely melted.
3. Upon melting of the reagents, the bath or reaction temperature was reduced to the target value of 120° C. and stirring started.
4. The air inside the flask was replaced with nitrogen using three vacuum/purging cycles.
5. The reaction was followed for 8 hours.
6. The nitrogen supply was then removed, and the pressure reduced using a vacuum pump set to a target of 15 mBars.

The reaction was followed until the targeted Mw (8000 about Da) and polydispersity (<2.5) were achieved. The trimethylolpropane ethoxylate: sebacic acid molar ratio targeted was 1:1, as confirmed by nuclear magnetic resonance (NMR).

Activation and Functionalization of PTS—Acrylation, Amination and Acidification (C2.1 to C2.4)

The PTS was reacted with acryloyl chloride (0.16 g of AcCl per 1 gram of PTS) in 10% (w/v) dichloromethane and triethylamine (0.19 g of TEA per 1 gram of PTS), thereby providing acrylated PTS (pre-polymer C2.1).

Ethanol capping of the acrylated PTSA was achieved by reaction with ethanol, overnight, at a temperature in the range of between 30 and 50° C.

The resulting polymer was purified by water washing and was distilled.

The acrylated PTS was reacted with diethylamine in dichloromethane (0.035 ml of DEA per 1 gram of C2.1) at 40° C. for 5 hours, thereby providing acrylated and aminated PTS (pre-polymer C2.2).

The resulting pre-polymer was acidified (0.04 ml of Acetic acid per 1 gram of C2.2) at room temperature for 15 minutes. The resulting pre-polymer (pre-polymer C2.3) was purified by water washing, brine washing and distillation.

Additives were added (Irgacure TPO photoinitiator), and the product was purified by solvent evaporation. The composition comprising pre-polymer C2.4 is a composition according to the invention.

Example 8: Dual Activation and Functionalization of PGS (C1.11 and C1.12)

Synthesis of PGS (C1.0)

Synthesis of PGS was done as presented in Example 1.

Activation and Functionalization of PGS— Dual Acrylation Followed by Amination and Acidification The following procedure was used to activate and functionalize hydroxy groups on the polymer backbone:

The PGS (C1.0) was reacted with 2-isocyanatoethyl acrylate (0.14 g/g of C1.0) and 2-isocyanatoethyl methacrylate (0.32 g/g of C1.0) in 20% (w/V) ethyl acetate at 70° C. for 16 h under magnetic stirring leading to C1.11.

The reaction mixture was then cooled down to ambient temperature. In a second step it was heated to 55° C. and diethylamine (0.15 g/g of C1.0) was added. The mixture was stirred at 55° C. for 5 h. The mixture was cooled down to ambient temperature and acetic acid (0.18 g/g of C1.0) was added to the mixture and stirred for 5 min. The product was purified by brine washings, dried with $MgSO_4$ and filtered. The resulting solution was concentrated to 50% (w/w). Additives were added (Irgacure TPO photoinitiator, and radical inhibitor MEHQ), and the product was purified by $scCO_2$ extraction.

The proportion of groups that include a positively charged nitrogen atom (DN+) and the proportion of groups that include a methacrylate group (DA) were measured using $^1H$ NMR spectroscopy. The DN+ was 0.44 mol/mol of polyacid, and the DA was 0.18 mol/mol of polyacid. This final product comprising pre-polymer C1.12 is a composition according to the invention.

Example 9: Acrylate Functionalization with Variation on the Acidification Process Acrylated PGS (C1.1) was reacted with diethylamine (66 mg of diethylamine (DEA) per 1 gram of acrylated PGS) in dichloromethane at 40° C. for 5 hours, thereby providing aminated and acrylated PGS (C1.3).

The aminated PGSA was acidified with acetic acid (6 molar equivalents compared to DEA) at room temperature for 15 minutes. The product was purified by brine washings and distillation.

Additives were added (Irgacure TPO photoinitiator, and radical inhibitor MEHQ), and the product, C1.17, was purified by $scCO_2$ extraction. The proportion of groups that include a positively charged nitrogen atom (DN+) and the proportion of groups that include an acrylate group (DA) were measured using $^1H$ NMR spectroscopy. The final DN+ was 0.21 mol/mol of polyacid, and the final DA was 0.30 mol/mol of polyacid. The final product comprising pre-polymer C1.17 is a composition according to the invention.

Example 10: Acrylate Functionalization with a Further Variation on the Acidification Process Acrylated PGS (C1.1) was reacted with diethylamine (66 mg of diethylamine (DEA) per 1 gram of acrylated PGS) in dichloromethane at 40° C. for 5 hours, thereby providing aminated and acrylated PGS (C1.3).

The aminated PGSA was washed with 1M HCl Brine (5 min under stirring before phase separation). The organic layer was then washed twice with brine. The organic layer was isolated, dried with $MgSO_4$ and concentrated to 50% (w/w).

Additives were added (Irgacure TPO photoinitiator and radical inhibitor MEHQ), and the product, C1.18, was purified by $scCO_2$ extraction. The proportion of groups that include a positively charged nitrogen atom (DN+) and the proportion of groups that include an acrylate group (DA) were measured using $^1H$ NMR spectroscopy. The final DN+ was 0.21 mol/mol of polyacid, and the final DA was 0.31 mol/mol of polyacid. The final product comprising pre-polymer C1.18 is a composition according to the invention.

Example 11: Acrylate Functionalization with a Yet Further Variation on the Acidification Process Acrylated PGS (C1.1) was reacted with diethylamine (46 mg of diethylamine (DEA) per 1 gram of acrylated PGS) in dichloromethane at 40° C. for 23 hours, thereby providing aminated and acrylated PGS (C1.3).

The aminated PGSA was acidified with formic acid (2 molar equivalents compared to DEA) at room temperature for 5 min under stirring.

Additive was added (Irgacure TPO photoinitiator), and the product, C1.19, was concentrated down under reduced pressure. The proportion of groups that include a positively charged nitrogen atom (DN+) and the proportion of groups that include an acrylate group (DA) were measured using $^1H$ NMR spectroscopy. The final DN+ was 0.16 mol/mol of polyacid, and the final DA was 0.30 mol/mol of polyacid. The final product comprising pre-polymer C1.19 is a composition according to the invention.

Adhesion Performance

Examples were tested for pull-off adhesion according to the following pull off method. Pull-off adhesion testing (at 90°) was performed on an Instron with fresh porcine epicardial tissue. The tissue was kept in phosphate-buffered saline to assure that it remained wet during testing. Unless specified, a poly glycerol sebacate urethane (PGSU) patch was used for testing and was about 200 mm thick and 6 mm in diameter. A thin layer of pre-polymer, with a thickness of about 200 μm, was applied to the patch material before adhesion testing. During the curing process, a compressive force of 3 N was applied to the sample composition coated patch with a non-adhesive material (borosilicate glass rod 9 mm in height) connected to the UV light guide (Lumen Dynamics Group Inc) with standard adhesive tape around both the glass rod and the light guide. The interposition of the borosilicate glass rod facilitates the release of the curing system from the patch without disturbing the patch/adhesive-tissue interface. The pull-off procedure involved grip separation at a rate of 8 mm/min, causing uniform patch detachment from the tissue surface. Adhesion force was recorded as the maximum force observed before adhesive failure, when a sharp decrease in the measured stress was observed.

Adhesion values for cured compositions prepared from pre-polymers described above are provided in table 1 below:

TABLE 1

| Cured material | DA | DN+ | Adhesion on heart tissue (N/$cm^2$) | Zeta (mV) |
|---|---|---|---|---|
| C1.2 | 0.45 | 0 | 0.4 ± 0.2 | NA* |
| C1.3 | 0.31 | NA | 1.0 ± 0.7 | NA* |
| C1.4 (example 1) | 0.31 | 0.18 | 7.1 ± 2.4 | 16 ± 6 |
| C1.4 (example 2) | 0.29 | 0.21 | 8 ± 4.3 | NA |
| C1.5 | 0.39 | 0.20 | 9.4 ± 2.5 | 27 ± 9 |
| C1.6 | 0.74 | ND | 5.0 ± 2.0 | ND |
| C1.7 | 0.28 | 0.15 | 7.4 ± 3.8 | 21 ± 6 |
| C1.8 | 0.3 | 0.1 | 7.2 ± 2.5 | 19 ± 5 |
| C1.10 | 0.30 | 0.19 | 6.8 ± 2.2 | NA |
| C2.1 | 0.51 | 0 | 0.7 ± 0.7 | −27 ± 6 |
| C2.4 | 0.40 | 0.15 | 6.9 ± 3.3 | 26 ± 8 |
| C1.12 | 0.44 | 0.18 | 7.6 ± 0.9 | ND |
| C1.17 | 0.30 | 0.21 | 7.9 ± 1.6 | ND |
| C1.18 | 0.31 | 0.21 | 6.6 ± 2.1 | ND |
| Cl.19 | 0.3 | 0.16 | 5.8 ± 1.5 | ND |

*Zeta potential of pre-polymers C1.2, C1.3 cannot be measured because the polymers are too hydrophobic to dissolve in the appropriate media for the measurements.

The table above shows that the adhesion values achieved using cured compositions according to the invention (C1.4, C1.5, C1.6, C1.7, C1.8, C1.10, C2.4, C1.12, C1.17, C1.18, C1.19) were better than the adhesion values achieved using cured compositions not according to the invention (C1.2, C1.3, C2.1).

Zeta Potential Compared to Adhesion

The zeta potential of pre-polymers according to the invention was measured using the protocol described above. The adhesion of cured compositions based on the pre-polymers was measured using the pull-off adhesion test described above. FIG. 1 shows the zeta potential results plotted against the adhesion results. The results show an improvement in adhesion as the zeta potential of the composition increases.

Example 12: Composition Formulations: Polymer Crosslinking Via Redox (C1.13 to C1.16)

Compositions were formulated using the pre-polymers C1.4 and C1.12 prepared as described above. The formulations are summarized in table 2 below:

TABLE 2

| Composition | C1.13 | C1.14 | C1.15 | C1.16 |
|---|---|---|---|---|
| Pre-polymer | 800 mg C1.4 | 800 mg C1.4 | 800 mg C1.4 | 800 mg C1.12 |
| Oxidant | 5.6 mg BPO | 9.8 mg BPO | 9.8 mg BPO | 9.8 mg BPO |
| Reducer | 7.8 mg MHPT | 14.1 mg MHPT | 14.1 mgTMA | 14.1 mgTMA |
| Oxygen inhibitor | — | — | 7.5 mgDPPS | 7.5 mg DPPS |
| Working time agent | 0.1 mg Tempol | 0.4 mg Tempol | 0.4 mg Tempol | 0.4 mg Tempol |
| Total wt % based on wt of composition | 1.8% | 3.3% | 3.9% | 3.9% |

BPO is benzoyl peroxide. MHPT is N-Methyl-N-(2-hydroxyethyl)-p-toluidine. TMA is 4-N,N Trimethylaniline.

DPPS is 4-(Diphenylphosphino)styrene. Tempol is 4-hydroxy-2,2,6,6-tetramethylpiperidin-1-oxyl.

A lap-shear adhesion performance test was used, for examples, C1.13, C1.14, C1.15 and C1.16 and for pre-polymer C1.4.

The protocol was adapted from ASTM F2255.1422857-1 entitled "Standard Test Method for Strength Properties of Tissue Adhesives in Lap-Shear by Tension Loading" and was as follows:

Porcine rump was used as biological tissue, sourced from local butchers, stored in the fridge (2-5° C.) and tested in lap-shear on the same day.

Muscle tissue was cut with knife and scalpel to obtain rectangular samples of the following dimensions: 1=3 cm, w=1.5 cm, h=0.2-0.4 cm. Tissue samples were kept in PBS until being tested (max 2 h).

For each test, two pieces of muscle were removed from PBS, deposited on a paper towel for 3 seconds on each side to remove excess of water. The tissue was still very wet.

The product to be tested was deposited with a spatula on one extremity of a muscle sample, to have a width of product around 0.8-1.0 cm, as close as possible from the border. The other muscle sample was then deposited on top to have an overlap of 1.5 cm x 0.8-1.0 cm.

The two muscle samples were put in contact by pressing the upper one in contact with the lower one, gently with a finger.

For light-activated formulations (e.g., C1.4 in the table below): The product was cured using the Omnicure Light (5 seconds cycles, 70% intensity). The overlap region was exposed to the light for at least 6 cycles.

For redox formulations: Wait until the products left-over in the microtube was fully cured.

For all samples:

The assembly was placed in the grips, vertically, starting from the upper grip. The lower grip was tightened, without pulling on the tissue.

Displacement and load were set to zero, then the upper grip went up at a rate of 5 mm/min until detachment of the two muscle samples. The load vs displacement curve was recorded and the maximum load before detachment was noted.

The area of product was measured with a caliper at the end of the test. It is easy to measure as the product is blue and does not break into pieces during testing.

The maximum load (in N) and area under the curve (mJ) were then divided by the area of polymer ($cm^2$) in the overlap area. This is the apparent shear strength (N/$cm^2$) and apparent AUC (mJ/$cm^2$).

At least 4 replicas are taken. The average and standard deviations were calculated.

The results are shown in table 3:

TABLE 3

| | Shear strength ($N/cm^2$) |
|---|---|
| C1.4 | 1.11 ± 0.56 |
| C1.13 | 1.49 ± 0.24 |
| C1.14 | 1.62 ± 0.38 |
| C1.15 | 1.18 ± 0.26 |
| C1.16 | 1.24 ± 0.47 |

The invention claimed is:

1. A composition comprising:

a pre-polymer having activated and functionalized groups on a polymeric backbone, wherein the composition has a zeta potential in the range of from 0 to 45 mV, wherein the polymeric backbone of the pre-polymer is of a formula $(\text{-A-B—})_n$, where A is derived from a substituted or unsubstituted polyol and B is derived from a substituted or unsubstituted polyacid, n is greater than 1, and wherein (a) the polyol is a triol and B is a diacid selected from glutaric acid, adipic acid, pimelic acid, sebacic acid and azelaic acid, or (b) the polyol is a diol and B is a triacid, wherein the activated functionalized group on the polymeric backbone of the pre-polymer is an acrylate group containing the structure $—C(=O)—CR_p=CR_qR_r$, wherein $R_p$, $R_q$, $R_r$ are independently from one another, selected from the group consisting of H, alkyl, aryl, substituted alkyl, substituted aryl, carboxylic acid, ester, amide, amine, urethane, ether, and carbonyl.

2. The composition according to claim 1, wherein the zeta potential is in the range of from about 5 to about 40 mV.

3. The composition according to claim 1, wherein the activated functionalized groups include a charged atom obtained by reacting an activated group with a compound containing a charged or chargeable atom.

4. The composition according to claim 3, wherein the proportion of activated functionalized groups that include a charged atom compared to the number of monomer units-A-B-in the backbone is from 0.05 to 0.4 mol/mol of monomer unit.

5. The composition according to claim 3, wherein the activated functionalized groups having a charged atom are groups having a positively charged heteroatom.

6. The composition according to claim 5, wherein the positively charged heteroatom is a positively charged nitrogen, phosphorus or sulfur atom.

7. The composition according to claim 6, wherein the activated functionalized groups including a positively charged nitrogen atom are of formula (III):

(III)

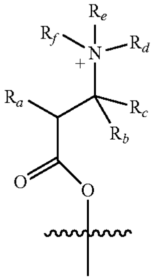

wherein $R_a$, $R_b$, $R_c$, $R_d$, $R_e$ and $R_f$ are independently selected from H, alkyl, alkenyl and aryl.

8. The composition according to claim 1, wherein the triol is selected from glycerol or trimethylolpropane ethoxylate.

9. The composition according to claim 1, wherein the diol is octanediol.

10. The composition according to claim 9, wherein the triacid is citric acid.

11. The composition according to claim 1, wherein the pre-polymer is of formula (VII):

(VII)

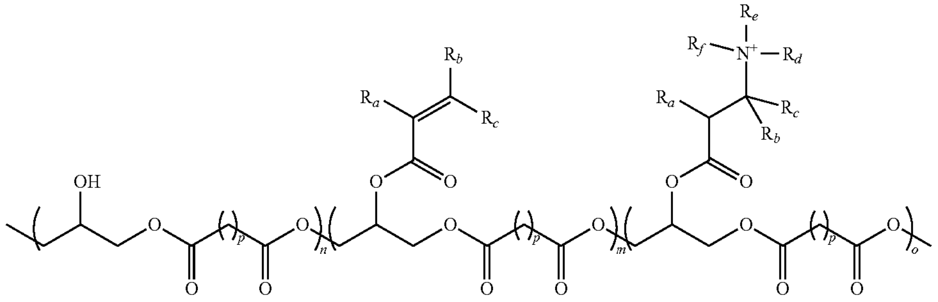

wherein p is between 3 and 8, wherein n, m and o are integers greater than 1, and wherein $R_a$, $R_b$, $R_c$, $R_d$, $R_e$ and $R_f$ are independently selected from H, alkyl, alkenyl and aryl.

12. A composition according to claim 11 further comprising an initiator.

13. A method for preparing a composition according to claim 1, comprising steps of:

i) polymerization of monomers to provide the pre-polymer backbone;

ii) activation of the backbone monomer units to provide the activated pre-polymer wherein the activation is achieved by acrylation of the hydroxy groups to give acrylate groups; and iii) functionalization of the activated pre-polymer with a compound containing a charged or chargeable atom to provide the activated and functionalized pre-polymer.

14. A method according to claim 13, wherein the functionalization in step iii) is achieved by reaction of the acrylate groups with an amine to give an amine group and acidification of the resulting amine to give an ammonium group.

15. A method according to claim 13, wherein the acrylation is achieved by reaction with acryloyl chloride.

16. A method according to claim 14, wherein the amine is selected from diethylamine, triethylamine, diisopropylethylamine, dibutylamine and piperidine.

17. A method of adhering tissue, comprising:

contacting the composition of claim 1 with tissue to be adhered; and curing the composition, thereby adhering the tissue.

18. A method of a medical device to tissue, comprising:

contacting the composition of claim 1 with tissue and the medical device to which the tissue is to be adhered; and curing the composition, thereby adhering the medical device to the tissue.

19. The method of claim 17 or 18 wherein the composition comprises a photo-initiator and curing occurs with light.

20. A method of adhering tissue comprising:

contacting the composition of claim 11 with tissue to be adhered; and curing the composition, thereby adhering the tissue.

21. The composition according to claim 1, wherein the zeta potential is in the range of from about 5 to about 30 mV.

22. The composition according to claim 4, wherein the proportion of activated functionalized groups that include a charged atom compared to the number of monomer units-A-B-in the backbone is from 0.09 to 0.25 mol/mol of monomer unit.

23. The composition according to claim 5, wherein the positively charged heteroatom is a positively charged nitrogen atom.

24. The composition according to claim 7, wherein at least one of $R_d$, $R_e$ and $R_f$ is H.

25. The composition according to claim 11, wherein the pre-polymer has a weight average molecular weight from about 2,700 Daltons to about 5,300 Daltons.

26. The composition according to claim 25, wherein the zeta potential is in the range of from about 5 to about 30 mV.

27. The composition according to claim 26, wherein the proportion of activated functionalized groups that include a charged atom compared to the number of monomer units-A-B-in the backbone is from 0.09 to 0.25 mol/mol of monomer unit.

28. The composition according to claim 27, wherein the proportion of activated functionalized groups that include a charged atom compared to the number of monomer units-A-B-in the backbone is from 0.14 to 0.23 mol/mol of monomer unit.

29. The composition according to claim 11, wherein the pre-polymer has a weight average molecular weight from about 1,000 Daltons to about 1,000,000 Daltons.

30. A method of adhering a medical device to tissue, comprising:

contacting the composition of claim 11 with tissue and the medical device to which the tissue is to be adhered; and curing the composition, thereby adhering the medical device to the tissue.

31. A composition according to claim 12, wherein the initiator is a photo-initiator.

* * * * *